United States Patent [19]

Schrot

[11] 4,057,470
[45] Nov. 8, 1977

[54] USE OF RADIOISOTOPES FOR RAPID IDENTIFICATION OF MICROORGANISMS

[75] Inventor: Joseph R. Schrot, Silver Spring, Md.

[73] Assignee: Biospherics Incorporated, Rockville, Md.

[21] Appl. No.: 658,859

[22] Filed: Feb. 18, 1976

Related U.S. Application Data

[62] Division of Ser. No. 429,629, Dec. 28, 1973, Pat. No. 3,969,496.

[51] Int. Cl.$^2$ ............................................... C12K 1/04
[52] U.S. Cl. .................................. 195/127; 195/103.7; 195/139
[58] Field of Search ...................... 195/103.7, 103.5 R, 195/127, 139

[56] References Cited

U.S. PATENT DOCUMENTS

| | | | |
|---|---|---|---|
| 3,673,410 | 6/1972 | Waite | 195/103.7 |
| 3,772,154 | 11/1973 | Isenberg et al. | 195/103.5 R |
| 3,819,483 | 6/1974 | Kronick et al. | 195/127 |
| 3,844,894 | 10/1974 | Kronick et al. | 195/127 |
| 3,941,660 | 3/1976 | Mirsky | 195/103.7 |

Primary Examiner—Alvin E. Tanenholtz
Assistant Examiner—Robert J. Warden
Attorney, Agent, or Firm—Roylance, Abrams, Berdo & Kaul

[57] ABSTRACT

There is disclosed a process for the rapid identification of a microorganism and an apparatus for performing the method. The process comprises inoculating a number of different $^{14}C$ labeled substrates with an unknown organism, at least some of said $^{14}C$ labeled substrates being capable of being metabolized to $^{14}CO_2$ by certain specific microorganisms. The substrates are incubated for a time sufficient to cause metabolic breakdown of at least some of said substrates resulting in the production of $^{14}CO_2$ and analysis for radioactivity in the $^{14}CO_2$ which is evolved from those substrates which are metabolized is performed to determine which substrates are metabolized and which substrates are not metabolized by the unknown microorganisms. There is thereby obtained a substrate radiorespirometric profile for the unknown microorganisms which is compared to standard radiorespirometric profiles for known organisms to determine to which standard radiorespirometric profile the radiorespirometric profile for said unknown microorganisms corresponds.

The apparatus includes trays for incubating the organisms in a selection of substrates, the trays having covers for collecting the evolved $^{14}CO_2$, conveyor means for transporting the covers to particle detectors, drive means for stepwise advancing the covers to sequentially expose the collection zones thereon to the detectors, counters for accumulating records of radiation levels, a data file of organism and substrate profiles, and means for comparing the profiles with the accumulated counts.

6 Claims, 19 Drawing Figures

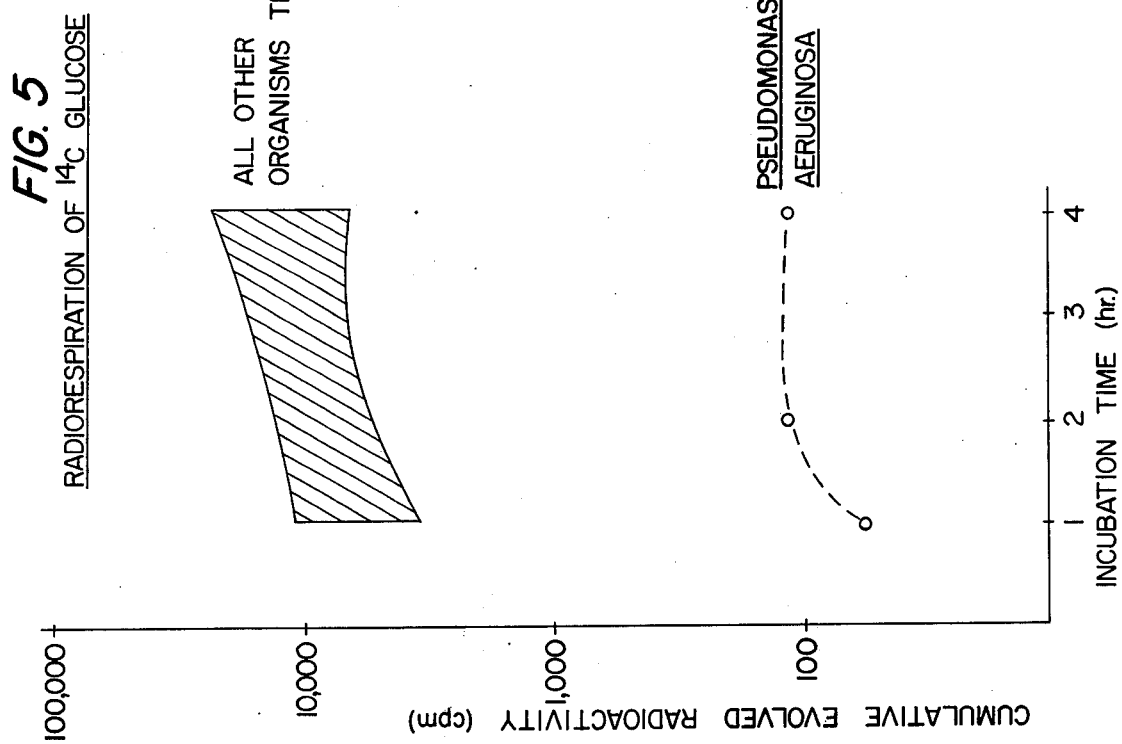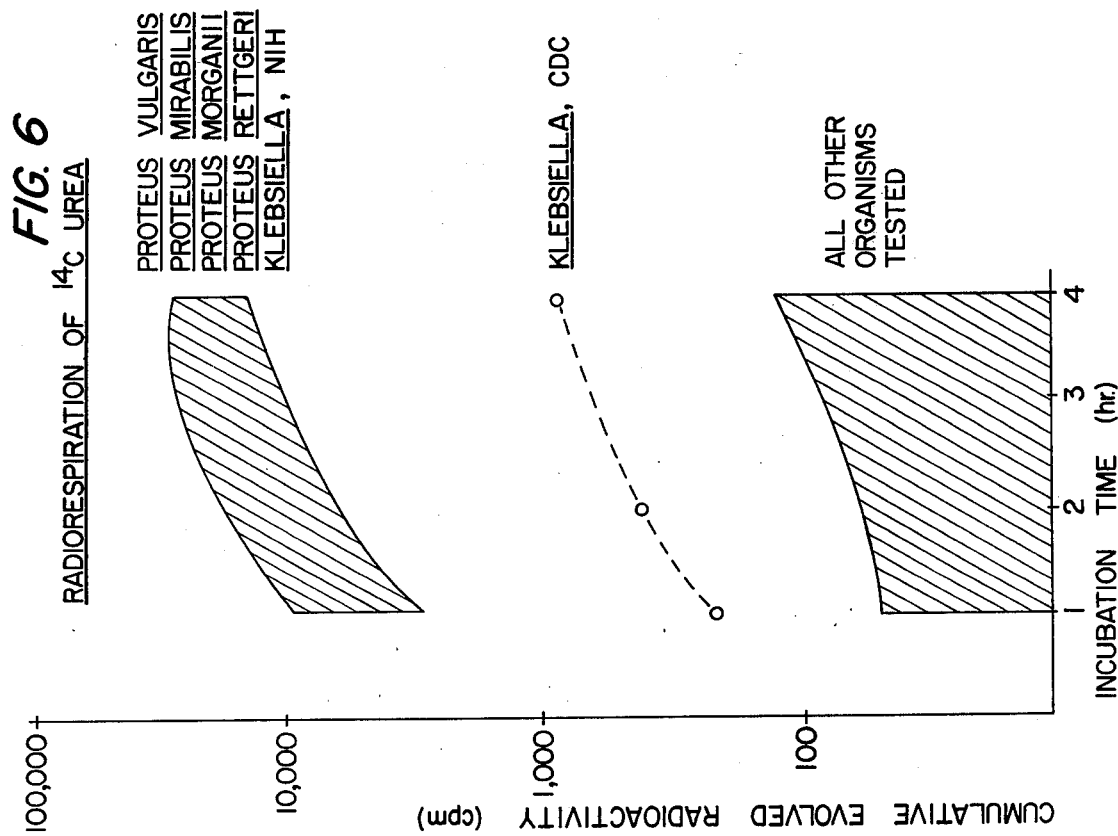

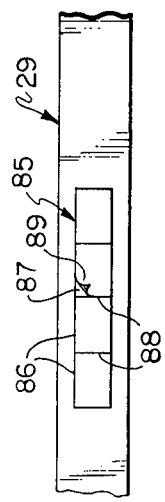
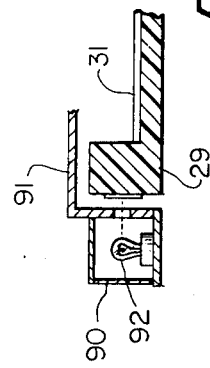
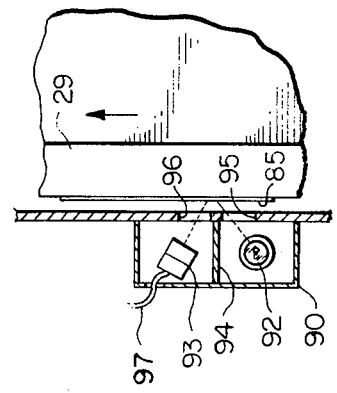
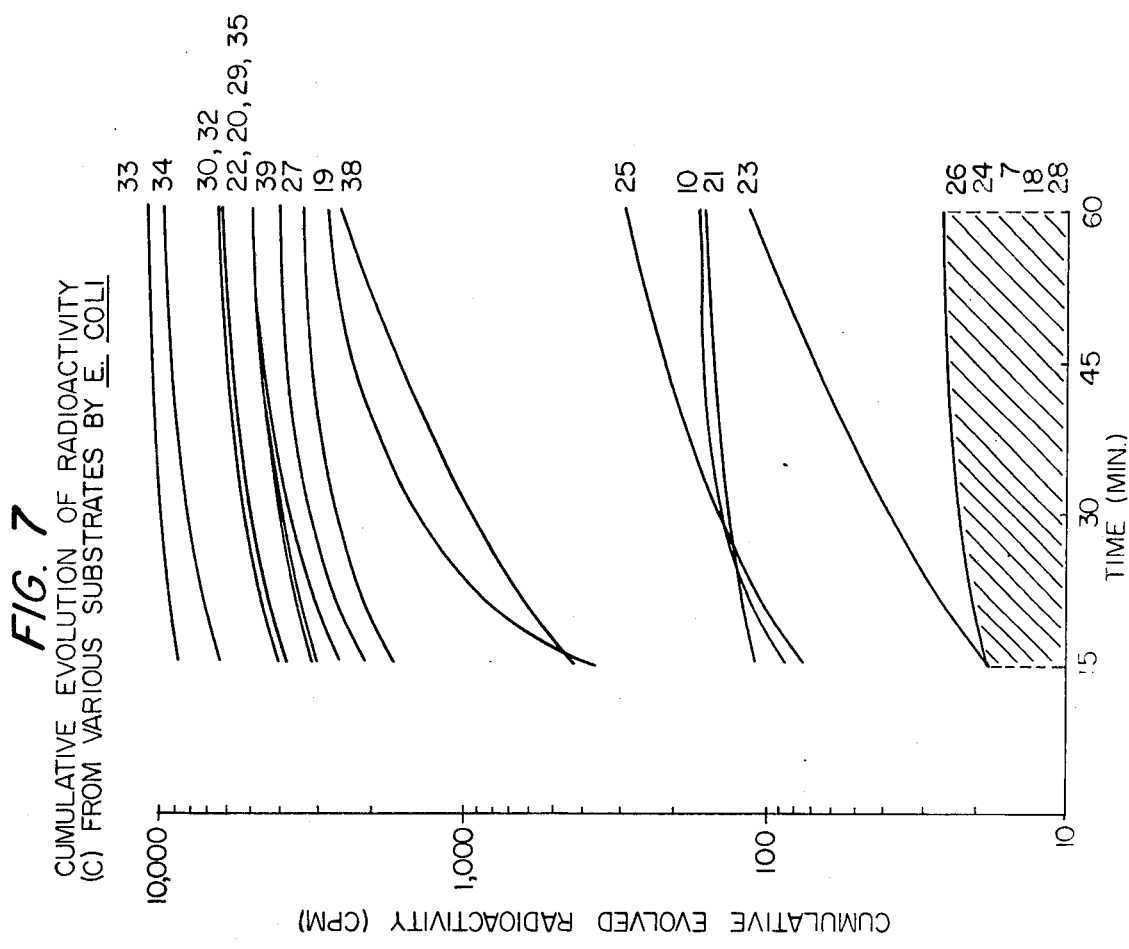

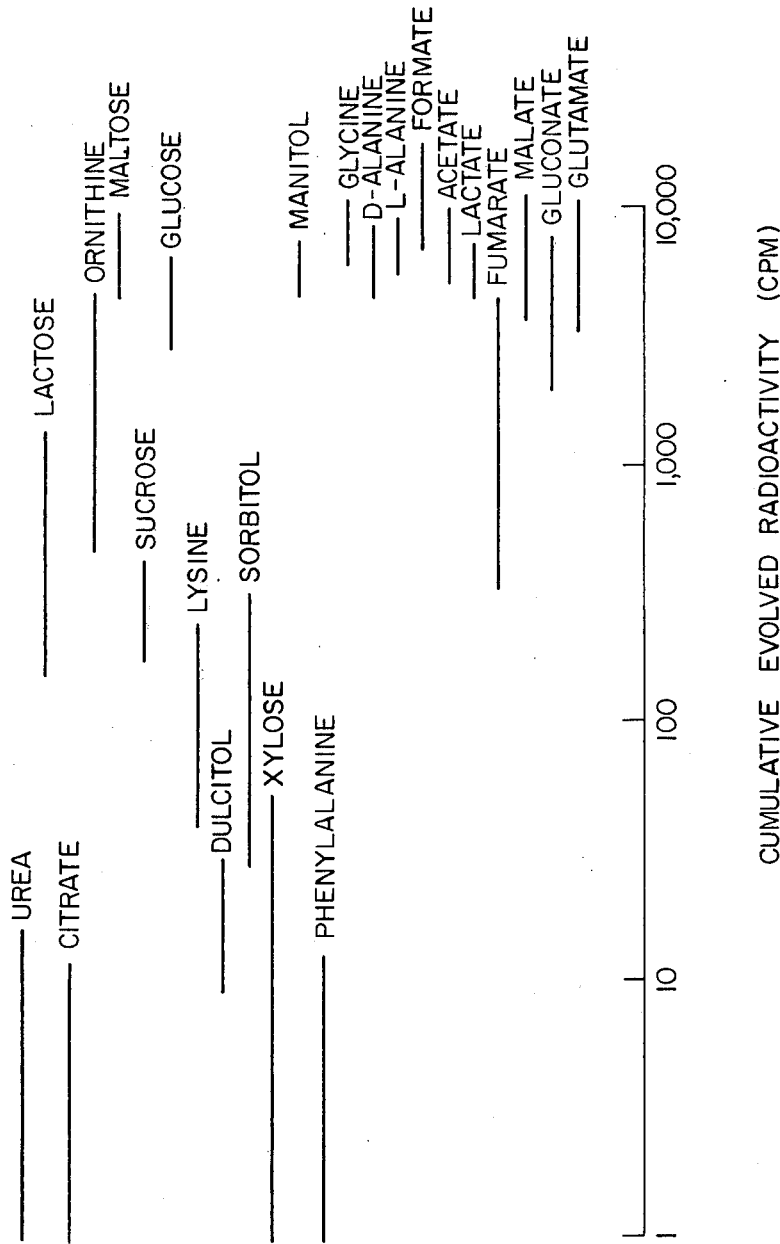

RANGE OF CUMULATIVE EVOLVED RADIOACTIVITY AFTER ONE-HOUR BY 12 REPETITIONS OF PROTEUS VULGARIS

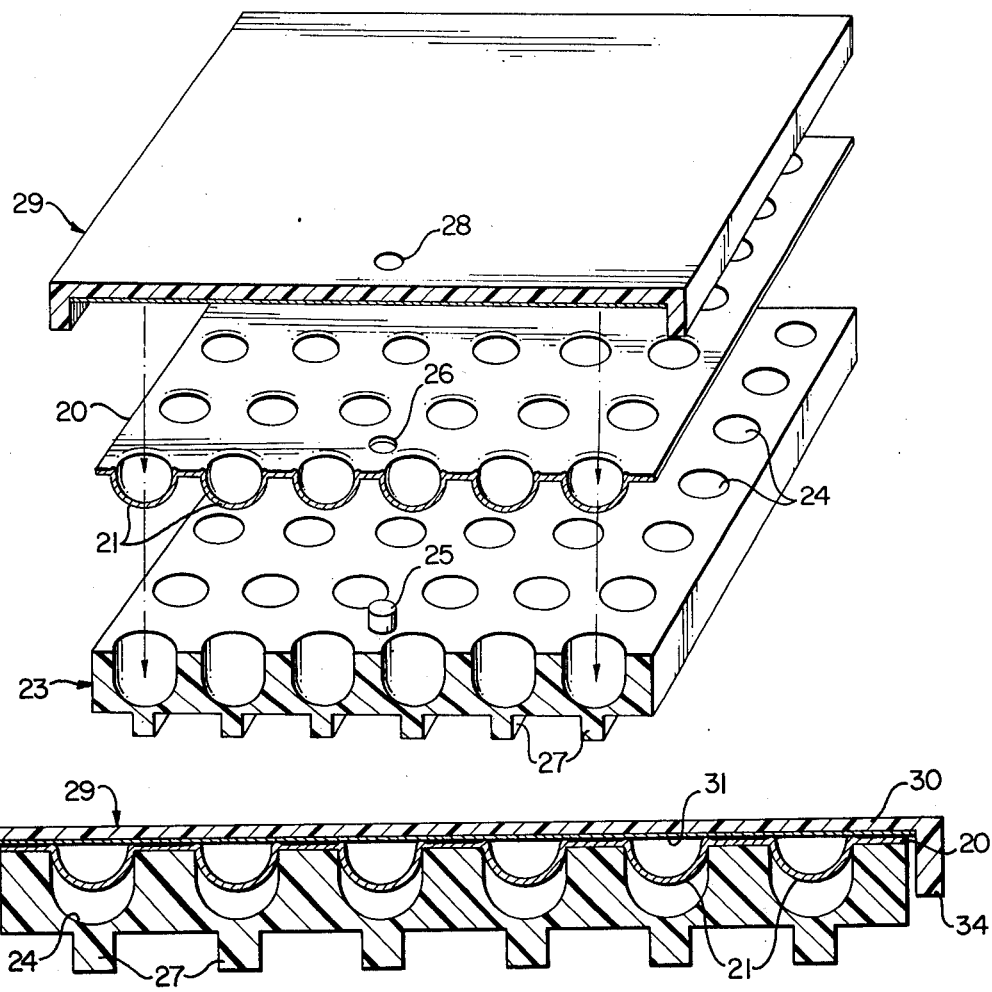
FIG. 10
FIG. 11
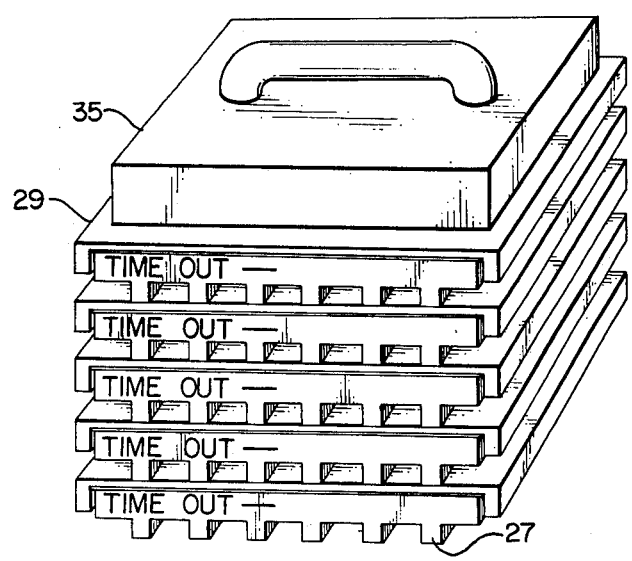
FIG. 12

USE OF RADIOISOTOPES FOR RAPID IDENTIFICATION OF MICROORGANISMS

This is a division of application Ser. No. 429,629, filed Dec. 28, 1973 now U.S. Pat. No. 3,969,496.

This invention relates to the use of radioisotopes for the rapid identification of microorganisms. More particularly, this invention relates to the identification of an unknown organism by obtaining a radiorespirometric profile of the unknown organism and comparing this radiorespirometric profile to standard radiorespirometric profiles obtained on known organisms to determine to which one it will correspond. By "radiorespirometric" is meant the measurement of metabolism of a microorganism which results in the evolution of radioactive gas from a radioactive substrate.

The term "microorganism" as used throughout this application refers to Orders I to X bacteria, mnycoplasma, actinomycetes and fungi which are listed in *Bergey's Manual of Determinative Bacteriology*, Seventh Edition, Williams & Wilkins Co., 1957, by Breed, Robert S., E.G.D. Murray and Nathan, R. Smith, the disclosure of which is incorporated herein by reference.

The conventional indentification of these microorganisms is a time-consuming and laborious process. Thus, for example, to identify an organism which is present in urine, stools, blood, spinal fluid, etc., the specimen is first streaked on agar plates or processed by other known techniques to obtain isolated colonies of the microorganism. After the unknown organism is isolated, it must then be subjected to a battery of tests to identify it. These tests include colony and cell morphology, stain characteristics, susceptibility to antimetabolites and serological and biochemical properties. Since many of the tests require relatively long incubation times, it frequently requires a minimum of 18 hours after isolation to arrive at a positive identification of the unknown microorganism. A method of microbial identification which would minimize the time required to make the identification would be an obvious advantage in the treatment of a patient since this would permit the attending physician to, e.g., prescribe the correct type and dosage of an antibiotic.

Rapid means for the identification of microorganisms would also be valuable in other areas such as to identify microorganisms present in food, drugs, spices, cosmetics, wine, beer, potable water, waste water, air, soil, etc.

Accordingly, it is a principal object of this invention to provide a means for the rapid identification of microorganisms.

According to the present invention, there is provided a process for the rapid identification of a microorganism which comprises inoculating a number of different $^{14}C$ specifically or uniformly labeled substrates, i.e., a substrate which contains at least some carbon atoms having an atomic weight of 14, with an unknown organism. Each of the $^{14}C$ labeled substrates is capable of being metabolized to $^{14}CO_2$ by certain specific microorganisms All of the substrates are then incubated for a predetermined length of time sufficient to cause breakdown of at least some of the substrates resulting in the production of $^{14}CO_2$.

Metabolism is defined as fermentative or oxidative metabolism via known and/or unknown pathways, which affects a $^{14}C$ atom of the substrate to produce $^{14}CO_2$. The extent of metabolism of substrates by the microorganism is determined by analyzing radioactivity which is evolved. If no $^{14}CO_2$ is evolved as indicated by the analysis for radioactivity, then it is known that those substrates are not metabolized at the $^{14}C$ atom to produce $^{14}CO_2$ by the particular unknown microorganism within the given incubation time. By determining the quantity of $^{14}CO_2$ produced from each $^{14}C$ labeled substrate, within a given time interval by the unknown microorganism, there is obtained a substrate radiorespirometric profile which serves as a fingerprint of the unknown microorganism. This radiorespirometric profile is then compared to standard radiorespirometric profiles which have been obtained in the same manner on known microorganisms. By determining which standard radiorespirometric profile the radiorespirometric profile of the unknown mircoorganism corresponds to, one is able to identify the unknown organism.

The process described hereinabove for the rapid identification of microorganisms by the use of radioisotopes may be conducted in an apparatus which comprises a means for containing a number of different and separate $^{14}C$ labeled substrates, means for inoculating each of the $^{14}C$ labeled substrates with an unknown microorganism, means for collecting radioactive gas which is produced as a result of metabolism of the $^{14}C$ labeled substrates and means for analyzing any gas obtained for radioactivity to determine whether metabolism occurred in each specific $^{14}C$ labeled medium.

The invention will be more fully described by reference to the accompanying drawings wherein:

FIGS. 5, 6 and 7 are graphs showing the rate and quantity of radioactive $CO_2$ gas evolved by different microorganisms in the presence of various $^{14}C$ labeled substrates;

FIGS. 8 and 9 illustrate the range of cumulative evolved radioactive $CO_2$ gas obtained in a series of repetitions of two different microorganisms on various substrates;

FIG. 10 is an exploded perspective view of an incubation unit assembly;

FIG. 11 is a side elevation, in section of the assembly of FIG. 10;

FIG. 12 is a perspective view of a plurality of the assemblies of FIGS. 10 and 11 stacked for incubation;

FIG. 17 is a side elevation of a portion of the tray of FIGS. 13 or 14;

FIG. 18 is a sectional view of a portion of the tray and guide rail of the apparatus of FIG. 15; and FIG. 19 is a partial plan view, in partial section of the apparatus of FIG. 18.

Figure 1:
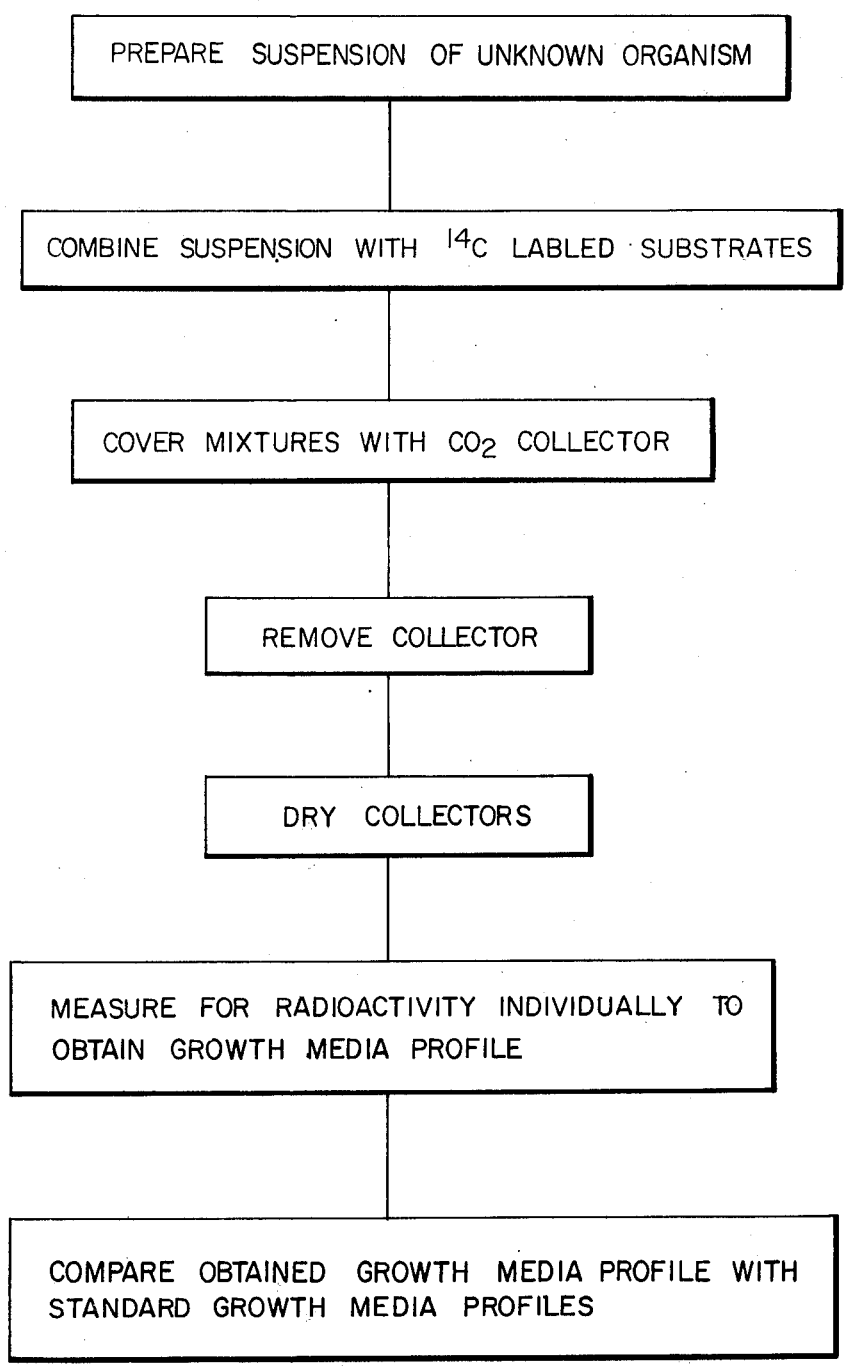
FIG. 1 is a flow diagram showing the process of this invention.
Figure 3:
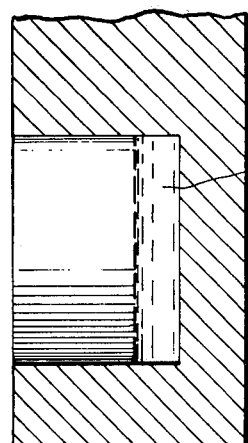
FIG. 3 is a sectional view taken along line 3-3 of FIG. 2.
Figure 4:
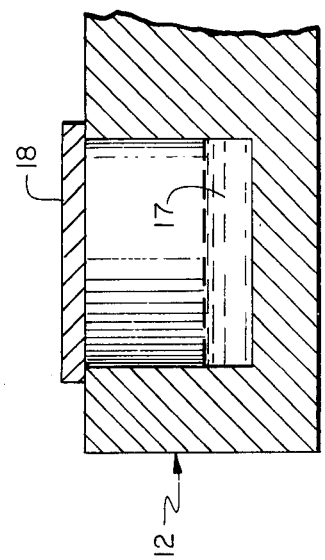
FIG. 4 is a view similar to FIG. 3 showing the tray in combination with a cover.
Figure 2:
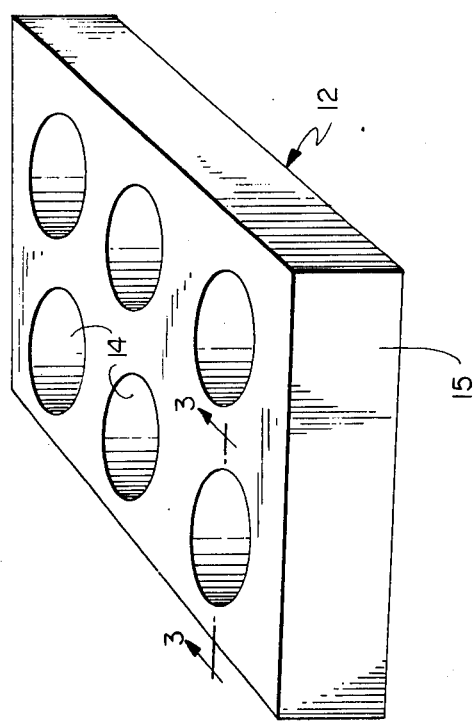
FIG. 2 is a perspective view of a microculture tray, partly in section, which may be used in the practice of this invention.

In accordance with the practice of this invention, standard radiorespirometric profiles are prepared for known microorganisms. Cultures of known microorganisms may be obtained from repositories such as the Center for Disease Control in Atlanta, Ga. (CDC) and American Type Culture Collection. Set forth in *Bergey's Manual of Determinative Bacteriology*, Orders I to X, are a number of microorganisms for which standard radiorespirometric profiles may be prepared. In some cases it may be sufficient to merely identify the microorganism by genus. However, in other cases, it may be desirable to identify the particular species of microorganism within the genus. Therefore, in accordance with this invention, it is sufficient that the radiorespirometric profile identify the microorganism as one which falls within a particular group which is differentiated from microorganisms falling within other groups. Species for which experimental data have been obtained include those microorganisms listed in Table 1.

TABLE 1

Escherichia coli
Alkalscens-Dispar
Shigella dysenteriae
Shigella, flexneri
Shigelli sonnei
Edwardsiella
Salmonella Gp B
Salmonella paratyphi A
Salmonella choleraesuis
Salmonella typhi
Salmonella pullorum
Salmonella galinarum
Arizona (lactose —)
Arizona (lactose +)
Citrobacter
Klebsiella pneumonia
Klebsiella ozaenae
Klebsiella rhinoschleromatis
Enterobacter aerogenes
Enterobacter hafnia
Enterobacter cloacae
Enterobacter liquefaciens
Serratia marcescens
Proteus vulgaris
Proteus mirabilis
Proteus morganii
Proteus rettgeri
Providencia alcalifacens
Providencia staurtii
Pseudomonas aeruginosa
Pectobacterium carotovarum
Haemophilus influensae
Streptococcus faecalis Each known organism is tested against a sufficient number of $^{14}C$ labeled substrates to differentiate it from other microorganisms. The substrate may contain one or more carbon atoms having an atomic weight of 14. Set forth in Table 2 are a number of $^{14}C$ labeled substrates which are commercially available and which have been tested. Each of the substrates set forth in Table 2 is assigned a numerical designation or numbering code which is used in FIG. 7. However, the identification method is not meant to be limited to only this list of substrates nor is the position of $^{14}C$ carbon atom specified, the only carbon atom which may be labeled and used for the identification method. In this table, the designation "UL" indicates that the substrate is uniformly labeled, i.e., the $^{14}C$ label is evenly distributed to all carbon atom positions on the molecule. The numerical designation (s) preceding the names of some substrates indicates the position of the $^{14}C$ atom(s). Most of the substrates listed in Table 2 are in the form of the sodium salt, although the free acid form or other forms may also be used.

Table 2

| Numbering Code | $^{14}C$ Labeled Substrates |
|---|---|
| 7 | UL $^{14}C$ urea |
| 10 | 1 $^{14}C$ lactose |
| 18 | 15 $^{14}C$ citrate |
| 19 | UL $^{14}C$ ornithine |
| 20 | UL $^{14}C$ maltose |
| 21 | UL $^{14}C$ sucrose |
| 22 | UL $^{14}C$ D-glucose |
| 23 | 1 $^{14}C$ DL-lysine |
| 24 | 1 $^{14}C$ dulcitol |
| 25 | UL $^{14}C$ sorbitol |
| 26 | UL $^{14}C$ D-xylose |
| 27 | UL $^{14}C$ D-manitol |
| 28 | 1 $^{14}C$ ring DL-phenylalanine |
| 29 | UL $^{14}C$ glycine |
| 30 | UL $^{14}C$ D-alanine |
| 31 | 2 $^{14}C$ xanthine |
| 32 | UL L-alanine |
| 33 | UL $^{14}C$ formate |
| 34 | UL $^{14}C$ acetate |
| 35 | UL $^{14}C$ DL-lactate |
| 38 | 1 $^{14}C$ fumarate |
| 39 | UL $^{14}C$ malate |
| 40 | 1 $^{14}C$ gluconate |
| 41 | UL $^{14}C$ glutamate |
| 42 | UL $^{14}C$ L-tyrosine |
| 43 | UL $^{14}C$ L-threonine |
| 44 | UL $^{14}C$ L-aspartic |
| 47 | 1 $^{14}C$ succinate |
| 48 | (ring 2 $^{14}C$) L-histidine |
| 49 | 2 $^{14}C$ (ring labeled) tryptophan |
| 50 | 1 $^{14}C$ DL-leucine |
| 51 | 1,3 $^{14}C$ glycerol |
| 52 | 1 $^{14}C$ D-galactose |
| 53 | 1 $^{14}C$ D-mannose |
| 54 | Carbonyl $^{14}C$ DL-methionine |
| 55 | 1 $^{14}C$ serine |
| 56 | 1,2 $^{14}C$ oxalate |
| 57 | 1 $^{14}C$ DL-valine |
| 58 | 1 $^{14}C$ malonate |
| 59 | 4 $^{14}C$ DL-aspartate |
| 60 | (guanido $^{14}C$) DL-arginine |
| 61 | UL $^{14}C$ trehalose |
| 62 | 2 $^{14}C$ uracil |
| 63 | UL $^{14}C$ erythritol |
| 64 | 1,4 $^{14}C$ DL-tartrate |
| 65 | (carbonyl $^{14}C$) dextran |
| 66 | UL $^{14}C$ starch |
| 67 | UL $^{14}C$ cellulose |
| 73 | 1 $^{14}C$ glucose |
| 74 | 6 $^{14}C$ glucose |
| 75 | 1 $^{14}C$ propionate |
| 76 | 1 $^{14}C$ butyric |

The production of $^{14}CO_2$ from some substrates, such as lactose, is dependent upon the induction of enzymes by that substrate and, therefore, is time dependent. It is preferred to use substrates for which breakdown to produce $^{14}CO_2$ is least time dependent--i.e., substrates which do not require inducible enzymes for breakdown or transport. The rapidness of the test is based upon constitutive enzymes which permit an organism to commence its action immediately. Conventional biochemical techniques utilize substrates which require many hours or days for metabolism. The radioisotopic procedure, therefore, does not conform to conventional results. Substrates which give positive fermentation results classically may be negative by the radiorespirometric method.

The media containing $^{14}C$ labeled substrates which are inoculated with the microorganisms may be composed of a basal medium containing salts, buffers, growth factors, preservatives and a single $^{14}C$ labeled substrate or may comprise simply aqueous solutions of the substrates. These $^{14}C$ labeled media may conveniently be contained in a compact, partitioned or welled tray such as a microculture tray as shown in FIGS. 2–5, or in a form separate from the microculture tray which is suitable for addition to the microculture tray. The substrates may be present in the wells of the tray in the form of liquid solutions, gels or in dry form--e.g., freeze dried. The substrate should be present in sufficient amount to provide a readily detectable amount of $^{14}CO_2$ upon metabolism. Preferably, the substrate in each $^{14}C$ labeled medium will contain at least four nanocuries of radioactivity.

A small amount of suspension of the microorganism is used to inoculate each of the different $^{14}C$ labeled media to form a mixture of the $^{14}C$ labeled medium and the organism. Inoculation may be performed by introducing the suspension of microorganism manually or by automated or mass replicating techniques. If the $^{14}C$ labeled substrate is present in dry form, the aqueous medium used to introduce the microorganism into the means for containing the $^{14}C$ labeled substrate reconstitutes the substrate and forms a mixture of the $^{14}C$ labeled medium and the organism.

Referring more specifically to FIGS. 2–5, there is shown a microculture tray 12 containing a plurality of wells 14. Each well 14 has a round bottom 15. The wells may be dimensioned so as to have a diameter of, for example, one-half inch and a height from top to bottom of one-half inch. Each well contains a medium 16 which includes a different $^{14}C$ labeled substrate. After the medium 16 in each well is inoculated with the suspension of microorganism to form a mixture 17 of the medium and the microorganism, the wells are then covered with a means for collecting radioactive $CO_2$ gas such as with a filter pad cover 18 containing a getter material, e.g., a solution of lithium hydroxide or barium hydroxide. The cover 18 should create a tight seal of the well 14. A separate disc-shaped cover can be used to cover each well or, alternatively, a single sheet can be used to cover all of the wells in the tray 12. All of the inoculated media are then incubated for a predetermined period of time, e.g., from 10 minutes to 4 hours. During this incubation period, if the $^{14}C$ labeled substrate contained in each medium is one which is metabolized by the organism, $^{14}CO_2$ will be evolved. This gas is collected by means of the cover 18. Thus, if the cover 18 contains barium hydroxide, the gas which is evolved will react with the barium hydroxide to form $Ba^{14}CO_3$ on the cover 18.

The covers 18 are then removed, dried and assayed for radioactivity. The instrument used for assaying for radioactivity can utilize several Geiger tubes which will monitor and record the presence of carbon atoms having an atomic weight of 14 contained on each of the covers 18-- e.g., a Gieger-Muller gas flow counter. The magnitude of radioactivity is measured for each of the getter covers and the results are recorded and used as a standard radiorespirometric profile for that organism. A specific system for accomplishing this is more fully discussed hereinafter.

A standard radiorespirometric profile may also be obtained by providing a radiorespirometric profile of an unknown organism in the manner previously described for known organisms. The unknown organism may then be identified by means of conventional biochemical methods for identification of unknown organisms. Thus, once the unknown organism has been positively identified by conventional means, the radiorespirometric profile for that organism may be used as a standard.

This invention may be used to identify microorganisms such as those belonging to the genera listed in *Bergey's Manual of Determinative Bacteriology*, Orders I-X, including various groups of pathogenic bacteria such as enterics, fastidious gram negative organisms, anaertobes, neisseria, gram positive cocci, Mima Herrilea Group, etc. A radiorespirometric profile is obtained for the unknown organism in the same manner as the standard radiorespirometric profiles are obtained. A pure culture is obtained from a sample of urine, blood, spinal fluid, food, water, air, etc. by streaking the sample material on an agar plate or by other known means. Incubation of these agar plates results in the growth of isolated colonies of organisms. Samples may then be taken from the individual colonies and suspended in an aqueous solution to prepare the inoculum for use in the practice of this invention.

The plates or other enrichment media used for obtaining the unknown organism from an isolation specimen frequently contain inhibitors for the growth of all microorganisms except certain species, so that only those species of microorganism which are not inhibited will grow. By the use of such inhibitors of the isolation specimens or in the $^{14}C$ labeled media, the isolation specimens may in certain cases be used directly for the inoculation of the $^{14}C$ labeled medium.

The size of the inoculum, i.e., the number of microorganism cells present in the mixture with the growth medium may vary over a relatively wide range without substantially influencing the results for a given substrate. It is, therefore, unnecessary to make precise and timeconsuming adjustments of inoculum size. In practice, the inoculum used in obtaining the data for FIGS. 5–9 was adjusted to an approximate optical density of 1.0. Moreover, the concentration of the substrate may be varied widely without substantially influencing the evolution of $^{14}CO_2$. Since large volumes of liquid retain significant quantities of $CO_2$, it is desirable to use a minimum amount of total liquid volume in performing each test--e.g., from about 0.05–0.2 ml.

The magnitude of response as measured by the amount of $^{14}CO_2$ evolved during the incubation reaction may be expressed in any suitable terms such as counts per minute. The results for a particular microorganism assayed against each substrate may be recorded on a card using lines or holes to indicate the magnitude of radioactive response so that a visual comparision may be made to a similar card prepared on an unknown organism. Alternatively, the data may be stored in the memory bank of a computer and the growth media profile obtained on an unknown organism may be matched by the computer to determine whether it falls within the ranges of response for the various standard radiorespirometric profiles. Statistical goodness of fit could be performed by the computer to give reliability of the identification. Further, they can be recorded simply as positive or negative--e.g, below a certain number of counts per minute, the response will be considered negative, and above that number of counts per minute the response will be considered positive. When the radiorespirometric profile for a given organism is expressed as either positive or negative against a given substrate, it may be necessary to utilize a larger number of substrates than when the radiorespirometric profile is expressed in actual numerical terms in order to differentiate it from radiorepirometric profiles for other microorganisms.

FIGS. 5 and 6 demonstrate how various species of microorganism produce a high level of $^{14}CO_2$ from $^{14}C$-glucose and $^{14}C$-urea, respectively, as opposed to others which produce only low level evolution of $^{14}CO_2$. Thus, in FIG. 5, all of the organisms set forth in Table 1 were tested under identical conditions against the substrate $^{14}C$-glucose. The failure of *P. aeruginosa* to produce substantial quantities of $^{14}CO_2$ from this substrate distinguishes it from the 29 other organisms tested.

Further, as shown in FIG. 6, testing of all of the organisms set forth in Table 1 against $^{14}C$ urea separated the genera of Proteus and Klebsiella from the remainder of the test group.

FIG. 7 shows the cumulative evolution of radioactivity from 21 different substrates tested against *E. coli*. The identifying number to the right of each curve refers to the identification of the substrate set forth in Table 3. Each curve was established by using three data points, one at 15, 30 and 60 minutes.

The data obtained for each of FIGS. 5, 6, 7 and 8 was obtained by adding an inoculum comprising 0.1 ml. or one drop of suspension containing $10^9$ cells of the various microorganisms per ml. of suspension. The inoculum was added to 0.1 ml. or one drop of substrate in microculture tray. The mixtures were then covered with getter covers and incubated for the time indicated. The getter covers were then dried and assayed for radioactivity.

Incubation time does not appear to be a critical factor. As shown in FIG. 7, most substrates produced similar results after 15 minutes as obtained after 60 minutes. However, the timing of tests for unknown is preferably about the same as used to establish standard radiorespirometric profiles.

Figure 9:
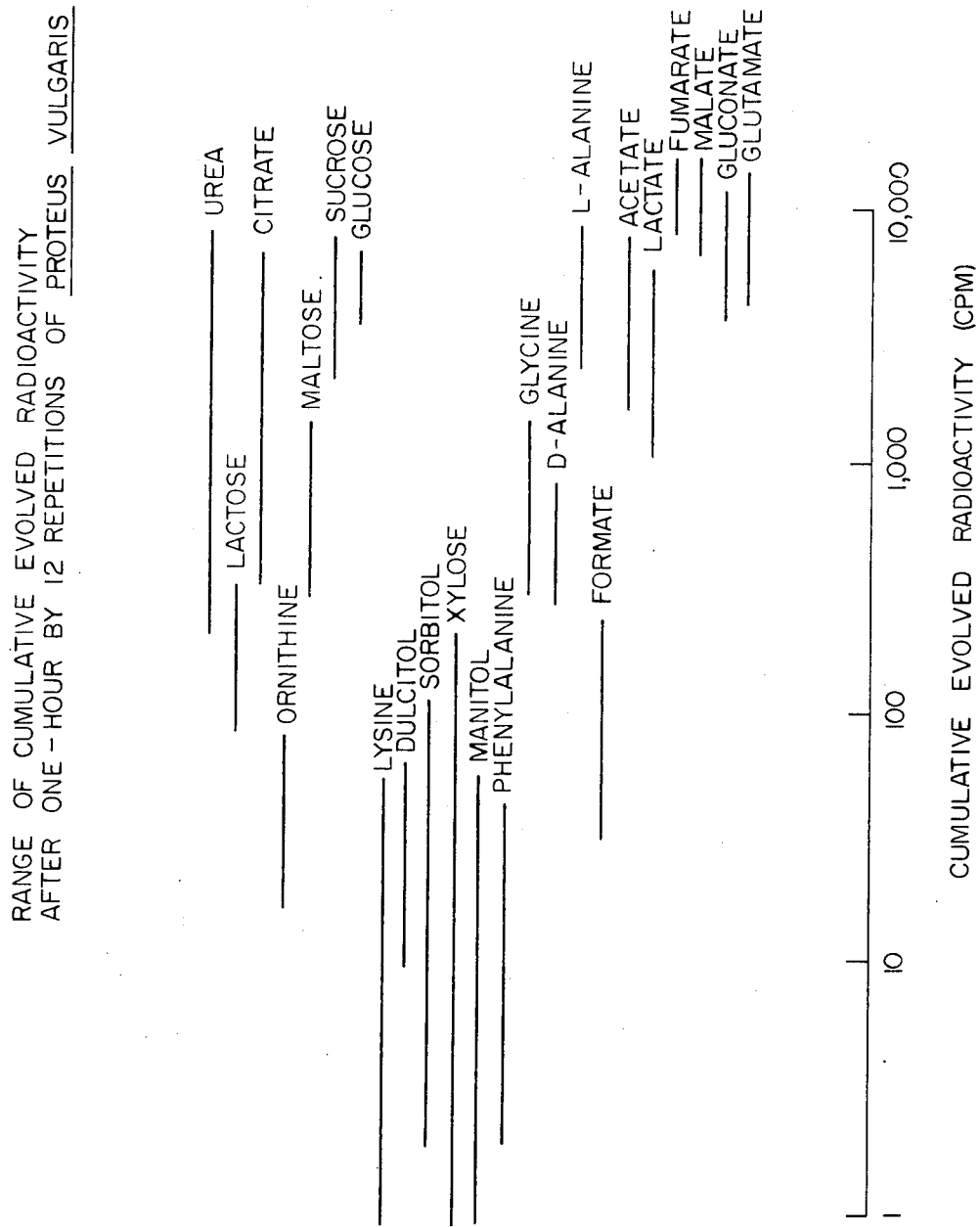

FIGS. 8 and 9 illustrate the variations which may occur in repeating assays for organisms against a number of different substrates. FIG. 8 shows the ranges of values obtained for five repetitions of *E. coli* assayed against each substrate after one hour of incubation, and FIG. 9 shows the ranges of values obtained for 12 repetitions of the bacterium *P. vulgaris* assayed after one hour of incubation against the various substrates.

Table 3 gives the radiorespirometric results obtained on 29 species of microorganisms. In this table the substrate is identified in the left hand column by the numbering code used in Table 2. The results set forth in Table 3 were obtained by inoculating the various substrates contained in wells of a microculture tray with one drop of an inoculum containing the microorganism, the suspension having an optical density of about 1 as measured on a spectrophotometer. The inoculum was added to one drop of each substrate and the mixture was covered with a getter cover containing $Ba(OH)_2$ and incubated for 1 hour. The getter covers were then dried and assayed for radioactivity. Several repetitions for each organism were run against the various substrates. The highest and lowest values obtained for each organism on each substrate are set forth in Table 3. Thus, Table 3 sets forth radiorespirometric profiles for each of these 29 species of microorganisms.

Table 3

| Substrate Code # | *Escherichia coli* 1 hr (cpm) | | *Alkalscens Dispar* 1 hr (cpm) | | *Shigella dysenteriae* 1 hr (cpm) | |
|---|---|---|---|---|---|---|
| | Low | High | Low | High | Low | High |
| 7 | <10 | 18 | | <10 | | <10 |
| 10 | 170 | 1,400 | 320 | 400 | 230 | 460 |
| 18 | <10 | 12 | | <10 | | <10 |
| 19 | 460 | 4,700 | 2,200 | 5,000 | <10 | 21 |
| 20 | 4,500 | 9,400 | 950 | 2,800 | 29 | 60 |
| 21 | 180 | 400 | 140 | 320 | 180 | 260 |
| 22 | 2,900 | 11,000 | 5,000 | 7,200 | 350 | 440 |
| 23 | 39 | 230 | 420 | 850 | | <10 |
| 24 | <10 | 30 | <10 | 64 | | <10 |
| 25 | 24 | 370 | 62 | 490 | <10 | 26 |
| 26 | <10 | 56 | <10 | 280 | | <10 |
| 27 | 5,600 | 11,000 | 2,900 | 6,600 | 320 | 610 |
| 28 | <10 | 12 | <10 | 25 | | <10 |
| 29 | 6,000 | 12,000 | 5,200 | 7,800 | 4,700 | 8,600 |
| 30 | 4,500 | 8,600 | 5,100 | 6,000 | 6,000 | 8,200 |
| 31 | | | | | | <10 |
| 32 | 5,000 | 9,000 | 3,800 | 6,200 | 1,400 | 4,600 |
| 33 | 7,900 | 22,000 | 11,000 | 20,000 | 12,000 | 14,000 |
| 34 | 5,200 | 14,000 | 150 | 200 | 48 | 170 |
| 35 | 4,600 | 7,400 | 4,200 | 5,100 | 300 | 590 |
| 38 | 330 | 12,000 | 4,600 | 11,000 | 8,500 | 16,000 |
| 39 | 1,700 | 12,000 | 4,500 | 8,400 | 4,500 | 11,000 |
| 40 | 1,600 | 11,500 | 3,200 | 5,000 | 210 | 230 |
| 41 | 3,200 | 17,000 | 3,600 | 8,000 | 8,000 | 8,600 |
| 42 | 300 | 380 | 270 | 450 | | |
| 43 | 280 | 420 | 3,900 | 6,200 | | |
| 44 | 6,600 | 9,300 | 5,000 | 6,200 | | |
| 47 | 66 | 88 | 5,200 | 8,000 | | |
| 48 | 60 | 85 | 380 | 400 | 500 | 550 |
| 49 | 150 | 850 | 160 | 240 | 240 | 270 |
| 50 | 34 | 140 | 36 | 58 | 20 | 36 |
| 51 | 14 | 120 | 62 | 68 | 17 | 30 |
| 52 | 340 | 660 | 260 | 530 | 200 | 270 |
| 53 | 1,900 | 7,200 | 2,600 | 3,200 | 1,800 | 2,700 |
| 54 | 140 | 220 | 62 | 140 | 170 | 200 |
| 55 | 5,200 | 14,000 | 4,000 | 5,900 | 1,900 | 2,000 |
| 56 | | | | | | |
| 57 | 290 | 1,000 | 140 | 260 | 860 | 1,000 |
| 58 | 110 | 260 | 22 | 64 | 400 | 430 |
| 59 | 3,500 | 10,500 | 1,600 | 2,100 | 1,500 | 2,600 |
| 60 | 3,500 | 4,800 | 2,600 | 3,200 | 510 | 630 |
| 61 | 170 | 1,100 | 6,300 | 6,900 | 550 | 750 |
| 62 | 25 | 340 | 38 | 68 | 92 | 140 |
| 63 | 36 | 170 | 19 | 63 | 23 | 35 |
| 64 | 180 | 1,200 | 32 | 42 | 280 | 480 |
| 65 | | | | | | |
| 66 | | | | | | |
| 67 | | | | | | |
| 73 | 940 | 1,400 | | | | |
| 74 | 1,600 | 3,000 | | | | |
| 75 | | | | | | |
| 76 | | | | | | |

| Substrate Code # | *Shigella flexneri* 1 hr (cpm) | | *Shigella sonnei* 1 hr (cpm) | | *Salmonella choleraesuis* 1 hr (cpm) | |
|---|---|---|---|---|---|---|
| | Low | High | Low | High | Low | High |
| 7 | | <10 | | <10 | | <10 |
| 10 | 400 | 500 | 460 | 520 | 400 | 500 |
| 18 | | <10 | | <10 | 5,700 | 7,400 |
| 19 | | <10 | 1,000 | 2,100 | 500 | 1,600 |
| 20 | 41 | 60 | 5,300 | 6,600 | 1,800 | 4,400 |
| 21 | 20 | 230 | 180 | 190 | <10 | 18 |
| 22 | 3,300 | 5,200 | 5,500 | 6,200 | 3,700 | 8,500 |
| 23 | | <10 | 60 | 72 | 37 | 84 |
| 24 | | <10 | 16 | 47 | | <10 |
| 25 | 70 | 170 | 90 | 180 | 800 | 1,100 |
| 26 | <10 | 26 | 36 | 41 | <10 | 21 |
| 27 | 3,700 | 7,600 | 5,900 | 6,700 | 2,200 | 6,500 |
| 28 | | <10 | | <10 | <10 | 18 |
| 29 | 6,400 | 7,900 | 7,300 | 11,000 | 6,000 | 7,000 |
| 30 | 5,100 | 9,000 | 7,900 | 11,500 | 7,000 | 11,000 |
| 31 | | | | | | |
| 32 | 5,700 | 6,000 | 4,900 | 10,500 | 3,800 | 7,400 |
| 33 | 13,000 | 15,000 | 11,000 | 18,000 | 11,000 | 20,000 |
| 34 | 140 | 180 | 2,200 | 2,300 | 8,000 | 15,000 |
| 35 | 3,800 | 11,000 | 12,000 | 16,000 | 5,200 | 8,100 |
| 38 | 8,000 | 14,000 | 14,000 | 16,000 | 11,000 | 12,000 |
| 39 | 8,100 | 8,800 | 9,000 | 11,000 | 8,600 | 16,000 |
| 40 | 950 | 1,400 | 2,200 | 4,700 | 7,200 | 8,100 |
| 41 | 5,800 | 6,400 | 7,800 | 9,500 | 11,000 | 12,000 |
| 42 | 180 | 190 | 660 | 880 | 400 | 460 |
| 43 | 6,000 | 6,500 | 7,200 | 8,400 | 8,900 | 14,000 |
| 44 | 6,300 | 6,600 | 7,600 | 12,000 | 6,100 | 8,000 |
| 47 | 9,500 | 10,000 | | | 12,000 | 19,000 |
| 48 | 450 | 530 | 410 | 820 | 430 | 540 |
| 49 | 250 | 620 | 75 | 160 | 78 | 120 |
| 50 | 330 | 420 | 32 | 140 | 54 | 71 |
| 51 | 40 | 60 | 13 | 82 | 15 | 50 |
| 52 | 880 | 3,300 | 580 | 1,800 | 270 | 800 |
| 53 | 1,900 | 2,700 | 2,000 | 5,600 | 2,300 | 3,300 |
| 54 | 130 | 160 | 95 | 230 | 110 | 140 |
| 55 | 2,500 | 4,700 | 5,400 | 8,900 | 7,000 | 8,300 |
| 56 | | 16 | | 82 | 51 | 53 |
| 57 | 450 | 750 | 90 | 270 | 38 | 140 |
| 58 | 100 | 160 | 68 | 120 | 30 | 61 |

Table 3-continued

| | | | | | | |
|---|---|---|---|---|---|---|
| 59 | 1,400 | 1,800 | 540 | 3,600 | 270 | 900 |
| 60 | 130 | 140 | 74 | 170 | 35 | 50 |
| 61 | 1,200 | 1,300 | 2,300 | 4,400 | 95 | 140 |
| 62 | 27 | 55 | 24 | 98 | 13 | 41 |
| 63 | 12 | 38 | 10 | 36 | <10 | 35 |
| 64 | 260 | 320 | 430 | 1,100 | 85 | 120 |
| 65 | | | | | | |
| 66 | | | | | | |
| 67 | | | | | | |
| 73 | | | | | | |
| 74 | | | | | | |
| 75 | | | | | | |
| 76 | | | | | | |

| Substrate Code # | Salmonella pullorum 1 hr. (cpm) | | Salmonella galinarum 1 hr. (cpm) | | Edwardsiella tarda 1 hr. (cpm) | |
|---|---|---|---|---|---|---|
| | Low | High | Low | High | Low | High |
| 7 | | <10 | | <10 | | <10 |
| 10 | 130 | 290 | 120 | 190 | 450 | 600 |
| 18 | 8,100 | 9,300 | 800 | 1,100 | 2,800 | 11,000 |
| 19 | 41 | 98 | 420 | 500 | 400 | 1,500 |
| 20 | 21 | 65 | 600 | 700 | 2,100 | 4,700 |
| 21 | 260 | 280 | 350 | 470 | 310 | 470 |
| 22 | 11,000 | 12,000 | 8,000 | 9,000 | 7,000 | 9,500 |
| 23 | 15 | 75 | 54 | 92 | 1,600 | 2,000 |
| 24 | <10 | 31 | <10 | 27 | <10 | 70 |
| 25 | 110 | 330 | 160 | 180 | 22 | 75 |
| 26 | <10 | 39 | 60 | 150 | <10 | 56 |
| 27 | 850 | 1,200 | 9,500 | 11,000 | 260 | 430 |
| 28 | <10 | 30 | <10 | 18 | | <10 |
| 29 | 1,100 | 1,400 | 1,100 | 4,600 | 2,200 | 4,200 |
| 30 | 1,300 | 1,700 | 11,000 | 14,000 | 170 | 760 |
| 31 | | | | | | |
| 32 | 1,100 | 1,400 | 10,000 | 18,000 | 840 | 3,700 |
| 33 | 300 | 380 | 880 | 950 | 560 | 13,000 |
| 34 | 910 | 1,100 | 8,200 | 10,500 | 9,000 | 12,000 |
| 35 | 680 | 780 | 350 | 420 | 850 | 5,200 |
| 38 | 1,200 | 1,700 | 9,700 | 13,000 | 11,500 | 14,000 |
| 39 | 1,200 | 1,700 | 5,300 | 13,000 | 7,500 | 12,000 |
| 40 | 230 | 430 | 4,100 | 8,100 | 2,900 | 12,000 |
| 41 | 1,000 | 1,700 | 10,000 | 17,000 | 9,000 | 14,000 |
| 42 | 620 | 690 | 310 | 460 | 3,400 | 4,500 |
| 43 | 710 | 1,300 | 1,500 | 2,700 | 7,000 | 8,000 |
| 44 | 1,300 | 1,500 | 12,000 | 15,000 | 9,500 | 11,000 |
| 47 | | | | | | |
| 48 | | | 380 | 2,800 | 4,500 | 5,600 |
| 49 | | | | | 580 | 650 |
| 50 | | | | | 81 | 95 |
| 51 | | | | | 51 | 71 |
| 52 | | | | | 210 | 250 |
| 53 | | | | | 1,100 | 1,200 |
| 54 | | | | | 55 | 74 |
| 55 | | | | | 1,600 | 2,600 |
| 56 | | | | | | |
| 57 | | | | | 170 | 230 |
| 58 | | | | | 35 | 95 |
| 59 | | | | | 150 | 210 |
| 60 | | | | | 52 | 58 |
| 61 | | | | | 73 | 96 |
| 62 | | | | | 42 | 48 |
| 63 | | | | | 12 | 42 |
| 64 | | | | | 5,800 | 9,900 |
| 65 | | | | | | |
| 66 | | | | | | |
| 67 | | | | | | |
| 73 | | | | | | |
| 74 | | | | | | |
| 75 | | | | | | |
| 76 | | | | | | |

| Substrate Code # | Arizona 1 hr. (cpm) | | Citrobacter freuendii 1 hr. (cpm) | | Klebsiella pneumonia 1 hr. (cpm) | |
|---|---|---|---|---|---|---|
| | Low | High | Low | High | Low | High |
| 7 | <10 | 35 | | <10 | 12 | 37 |
| 10 | 110 | 520 | 150 | 600 | 350 | 1,200 |
| 18 | 350 | 5,300 | 4,800 | 12,000 | 510 | 1,400 |
| 19 | 95 | 8,200 | 5,000 | 16,000 | 1,900 | 5,400 |
| 20 | 280 | 2,900 | 1,500 | 5,900 | 1,300 | 3,700 |
| 21 | 80 | 330 | 62 | 210 | 2,100 | 5,000 |
| 22 | 380 | 7,200 | 2,100 | 6,000 | 4,100 | 6,200 |
| 23 | 160 | 4,200 | 950 | 4,200 | 850 | 1,400 |
| 24 | <10 | 45 | | <10 | | <10 |
| 25 | 70 | 350 | 130 | 420 | 120 | 720 |
| 26 | 15 | 450 | 210 | 950 | 15 | 92 |
| 27 | 400 | 4,800 | 2,700 | 6,200 | 3,200 | 13,000 |
| 28 | <10 | 35 | | <10 | <10 | 36 |
| 29 | 500 | 8,500 | 4,700 | 8,200 | 2,100 | 7,500 |
| 30 | 1,800 | 8,500 | 4,100 | 9,200 | 3,500 | 7,500 |
| 31 | | | | | | |
| 32 | 1,300 | 8,500 | 5,800 | 11,000 | 4,800 | 8,500 |

| | | | | | | |
|---|---|---|---|---|---|---|
| 33 | 3,300 | 24,000 | 8,000 | 20,000 | 8,800 | 15,000 |
| 34 | 290 | 5,500 | 5,100 | 9,600 | 7,200 | 9,000 |
| 35 | 1,900 | 15,000 | 3,100 | 13,000 | 850 | 4,000 |
| 38 | 610 | 9,500 | 1,900 | 14,000 | 4,000 | 16,000 |
| 39 | 1,400 | 12,000 | 5,800 | 8,800 | 7,500 | 12,000 |
| 40 | 250 | 12,000 | | | 3,400 | 9,000 |
| 41 | 1,500 | 8,000 | | | 4,500 | 8,000 |
| 42 | | | | | 580 | 750 |
| 43 | | | | | 6,500 | 9,000 |
| 44 | | | | | 6,000 | 7,000 |
| 47 | 6,500 | 8,000 | 5,800 | 6,200 | 8,800 | 15,000 |
| 48 | 4,000 | 5,500 | 2,000 | 3,400 | 3,200 | 12,000 |
| 49 | 380 | 700 | 250 | 450 | 380 | 18,000 |
| 50 | 110 | 600 | 88 | 150 | 310 | 950 |
| 51 | 14 | 52 | <10 | 32 | <10 | 24 |
| 52 | 800 | 1,500 | 75 | 27 | 900 | 1,200 |
| 53 | 2,000 | 5,500 | 2,100 | 2,600 | 3,800 | 5,700 |
| 54 | 320 | 1,400 | 620 | 2,600 | 420 | 1,200 |
| 55 | 6,000 | 10,000 | 3,100 | 5,800 | 2,400 | 9,400 |
| 56 | | | | | | |
| 57 | 410 | 620 | 170 | 320 | 4,200 | 1,800 |
| 58 | 850 | 550 | 40 | 100 | 32 | 520 |
| 59 | 3,200 | 4,300 | 2,100 | 3,200 | 2,100 | 4,700 |
| 60 | 3,200 | 7,000 | 3,200 | 6,800 | 6,000 | 11,000 |
| 61 | 2,300 | 6,200 | 5,200 | 8,500 | 1,900 | 5,500 |
| 62 | 38 | 450 | 51 | 330 | 100 | 800 |
| 63 | 18 | 29 | 16 | 72 | 240 | 550 |
| 64 | 120 | 390 | 450 | 2,700 | 92 | 170 |
| 65 | | | | | | |
| 66 | | | | | | |
| 67 | | | | | | |
| 73 | | | | | | |
| 74 | | | | | | |
| 75 | | | | | | |
| 76 | | | | | | |

| Substrate Code 190 | Klebsiella ozaenae 1 hr. (cpm) | | Klebsiella rhinoschleromatis 1 hr. (cpm) | | Enterobacter cloacae 1 hr. (cpm) | |
|---|---|---|---|---|---|---|
| | Low | High | Low | High | Low | High |
| 7 | | <10 | | <10 | | <10 |
| 10 | 310 | 330 | 32 | 42 | 380 | 420 |
| 18 | | <10 | <10 | 16 | 4,100 | 6,200 |
| 19 | 3,200 | 5,100 | 34 | 65 | 4,000 | 5,500 |
| 20 | 500 | 980 | 2,100 | 2,500 | 2,000 | 2,300 |
| 21 | 81 | 170 | 180 | 230 | 3,400 | 5,000 |
| 22 | 4,000 | 4,600 | 4,700 | 6,500 | 5,500 | 8,500 |
| 23 | 1,100 | 2,300 | 140 | 160 | 410 | 1,400 |
| 24 | | <10 | <10 | 27 | <10 | 16 |
| 25 | 45 | 68 | 140 | 210 | 90 | 420 |
| 26 | 34 | 36 | 50 | 75 | <10 | 63 |
| 27 | 1,200 | 1,900 | 4,500 | 5,200 | 3,500 | 7,500 |
| 28 | 160 | 950 | | <10 | 32 | 75 |
| 29 | 4,800 | 5,200 | 3,200 | 3,700 | 4,600 | 6,500 |
| 30 | 4,500 | 9,500 | 200 | 250 | 5,500 | 7,500 |
| 31 | | | | | | |
| 32 | 5,500 | 7,400 | 5,000 | 9,000 | 5,500 | 7,500 |
| 33 | 12,000 | 22,000 | 5,000 | 15,000 | 10,000 | 14,000 |
| 34 | 9,000 | 12,500 | 9,200 | 12,000 | 5,500 | 8,000 |
| 35 | 12,000 | 15,000 | 6,200 | 7,500 | 6,200 | 7,000 |
| 38 | 11,000 | 12,000 | 9,500 | 11,000 | 7,800 | 12,000 |
| 39 | 10,000 | 12,000 | 7,500 | 14,000 | 8,000 | 9,100 |
| 40 | 7,500 | 9,500 | 6,000 | 6,500 | 6,100 | 6,700 |
| 41 | 7,000 | 12,000 | 8,800 | 12,000 | 10,000 | 11,000 |
| 42 | 1,600 | 2,700 | 340 | 410 | 2,400 | 2,600 |
| 43 | 5,100 | 9,500 | 6,200 | 10,000 | 8,800 | 9,000 |
| 44 | 6,600 | 11,000 | 8,000 | 9,000 | 7,000 | 7,500 |
| 47 | | | | | 7,000 | 11,000 |
| 48 | 5,200 | 10,000 | 4,100 | 4,800 | 3,200 | 7,800 |
| 49 | 410 | 730 | 300 | 740 | 310 | 1,200 |
| 50 | 410 | 800 | 45 | 170 | 1,200 | 6,500 |
| 51 | 35 | 65 | 32 | 85 | <10 | 700 |
| 52 | 320 | 590 | 1,100 | 1,500 | 480 | 1,500 |
| 53 | 520 | 830 | 1,800 | 2,800 | 3,000 | 9,500 |
| 54 | 150 | 300 | 58 | 120 | 200 | 8,100 |
| 55 | 650 | 950 | 4,500 | 6,400 | 4,200 | 11,000 |
| 56 | 180 | 220 | | | | |
| 57 | 310 | 420 | 130 | 400 | 3,300 | 28,000 |
| 58 | 100 | 170 | 48 | 130 | 780 | 1,300 |
| 59 | 2,200 | 5,700 | 3,300 | 5,600 | 1,700 | 4,100 |
| 60 | 5,800 | 7,000 | 35 | 150 | 2,100 | 12,000 |
| 61 | 1,200 | 1,800 | 1,500 | 2,000 | 2,300 | 4,900 |
| 62 | 60 | 180 | 58 | 92 | 2,100 | 7,200 |
| 63 | 33 | 65 | 40 | 82 | 780 | 2,200 |
| 64 | 280 | 350 | 110 | 200 | 320 | 580 |
| 65 | | | | | | |
| 66 | | | | | | |
| 67 | | | | | | |
| 73 | | | | | | |
| 74 | | | | | | |
| 75 | | | | | | |
| 76 | | | | | | |

Table 3-continued

| Sub-strate Code # | Enterobacter aerogenes 1 hr. (cpm) | | Enterobacter hafnia 1 hr. (cpm) | | Enterobacter liquefaciens 1 hr. (cpm) | |
|---|---|---|---|---|---|---|
| | Low | High | Low | High | Low | High |
| 7 | | <10 | | <10 | | <10 |
| 10 | 170 | 510 | 1,400 | 2,900 | 180 | 500 |
| 18 | 5,800 | 12,000 | 100 | 520 | 2,900 | 8,000 |
| 19 | 4,000 | 11,000 | 780 | 1,100 | 4,000 | 7,800 |
| 20 | 1,900 | 2,100 | 1,500 | 1,800 | 2,400 | 3,800 |
| 21 | 2,100 | 2,700 | 88 | 220 | 150 | 230 |
| 22 | 5,100 | 6,600 | 550 | 680 | 5,800 | 7,000 |
| 23 | 3,100 | 5,000 | 920 | 1,400 | 1,100 | 3,700 |
| 24 | <10 | 20 | | <10 | <10 | 61 |
| 25 | 13 | 28 | <10 | 17 | 160 | 500 |
| 26 | 11 | 56 | <10 | 2 | 51 | 140 |
| 27 | 3,200 | 7,500 | 20 | 1,200 | 1,900 | 4,400 |
| 28 | 550 | 600 | 450 | 700 | 320 | 1,300 |
| 29 | 3,000 | 9,000 | 7,000 | 8,000 | 5,500 | 9,500 |
| 30 | 4,700 | 9,500 | 4,100 | 8,200 | 5,500 | 9,500 |
| 31 | | | | | | |
| 32 | 6,000 | 11,000 | 4,800 | 7,200 | 7,500 | 12,000 |
| 33 | 11,000 | 19,000 | 8,500 | 17,000 | 13,000 | 18,000 |
| 34 | 4,800 | 9,800 | 4,700 | 5,200 | 5,300 | 12,000 |
| 35 | 2,400 | 11,000 | 2,200 | 8,500 | 2,500 | 4,100 |
| 38 | 5,400 | 10,000 | 8,100 | 11,000 | 7,100 | 13,000 |
| 39 | 5,500 | 11,000 | 6,800 | 7,700 | 8,200 | 11,000 |
| 40 | 10,000 | 11,000 | 9,000 | 9,500 | 5,000 | 9,500 |
| 41 | 11,000 | 12,000 | 4,400 | 7,500 | 8,000 | 12,000 |
| 42 | | | 5,100 | 5,500 | 4,500 | 6,200 |
| 43 | | | 5,100 | 5,500 | 6,800 | 9,500 |
| 44 | | | 7,200 | 7,500 | 7,400 | 9,000 |
| 47 | | | 9,900 | 10,500 | | |
| 48 | 3,800 | 5,600 | 3,200 | 7,800 | 506 | 900 |
| 49 | 880 | 960 | 4,800 | 9,600 | 560 | 950 |
| 50 | 210 | 460 | 1,200 | 5,300 | 460 | 730 |
| 51 | 23 | 40 | 30 | 52 | 31 | 67 |
| 52 | 210 | 480 | 320 | 1,100 | 310 | 350 |
| 53 | 260 | 380 | 2,100 | 3,500 | 1,200 | 1,700 |
| 54 | 320 | 400 | 600 | 900 | 300 | 450 |
| 55 | 9,500 | 11,000 | 4,400 | 9,500 | 4,200 | 7,000 |
| 56 | 25 | 36 | | | 320 | 420 |
| 57 | 110 | 220 | 1,800 | 3,000 | 230 | 430 |
| 58 | 43 | 73 | 130 | 590 | 60 | 180 |
| 59 | 2,100 | 3,600 | 4,500 | 8,500 | 3,200 | 9,500 |
| 60 | 2,500 | 4,500 | 60 | 3,400 | 2,700 | 5,200 |
| 61 | 950 | 2,700 | 950 | 3,000 | 750 | 1,200 |
| 62 | 15 | 59 | 50 | 390 | 42 | 580 |
| 63 | 12 | 31 | 120 | 270 | 31 | 280 |
| 64 | 550 | 620 | 380 | 1,100 | 410 | 490 |
| 65 | | | | | | |
| 66 | | | | | | |
| 67 | | | | | | |
| 73 | | | | | | |
| 74 | | | | | | |
| 75 | | | | | | |
| 76 | | | | | | |

| Sub-strate Code # | Pectobacterium carotovarum 1 hr. (cpm) | | Serratia marcescens 1 hr. (cpm) | | Proteus vulgaris 1 hr. (cpm) | |
|---|---|---|---|---|---|---|
| | Low | High | Low | High | Low | High |
| 7 | | <10 | | <10 | 220 | 9,000 |
| 10 | 850 | 950 | 230 | 420 | 95 | 350 |
| 18 | 8,500 | 13,000 | 4,300 | 5,100 | 350 | 7,500 |
| 19 | 95 | 140 | 3,500 | 4,000 | 18 | 85 |
| 20 | 65 | 120 | 3,500 | 4,000 | 310 | 1,600 |
| 21 | 6,100 | 6,800 | 3,500 | 4,800 | 2,200 | 8,500 |
| 22 | 8,000 | 9,000 | 6,300 | 8,200 | 3,800 | 7,800 |
| 23 | <10 | 22 | 850 | 1,800 | <10 | 58 |
| 24 | 28 | 88 | | <10 | <10 | 65 |
| 25 | 180 | 270 | 160 | 330 | <10 | 110 |
| 26 | 60 | 70 | | <10 | <10 | 220 |
| 27 | 5,500 | 8,000 | 3,500 | 8,000 | <10 | 60 |
| 28 | <10 | 32 | 150 | 600 | <10 | 45 |
| 29 | 650 | 700 | 6,500 | 7,000 | 310 | 1,700 |
| 30 | 900 | 1,000 | 5,000 | 7,000 | 290 | 900 |
| 31 | | | | | | |
| 32 | 620 | 920 | 5,800 | 8,000 | 2,500 | 9,500 |
| 33 | 12,000 | 13,000 | 11,000 | 17,000 | 32 | 250 |
| 34 | 9,000 | 11,000 | 5,500 | 12,000 | 1,600 | 8,500 |
| 35 | 1,800 | 2,600 | 2,200 | 6,800 | 1,100 | 6,200 |
| 38 | 7,000 | 8,000 | 3,100 | 7,500 | 8,500 | 17,000 |
| 39 | 4,800 | 6,200 | 6,500 | 10,500 | 7,200 | 17,000 |
| 40 | 2,300 | 2,600 | 5,500 | 6,000 | 3,800 | 13,000 |
| 41 | 12,000 | 18,000 | 8,500 | 13,000 | 4,500 | 16,000 |
| 42 | 500 | 600 | 5,800 | 6,200 | | |
| 43 | 500 | 600 | 8,000 | 9,000 | | |
| 44 | 11,000 | 14,000 | 8,000 | 9,000 | | |
| 47 | | | 9,000 | 10,000 | 5,000 | 6,000 |
| 48 | 1,100 | 3,100 | 4,800 | 9,800 | 320 | 850 |
| 49 | 280 | 390 | 3,909 | 9,200 | 180 | 700 |
| 50 | 78 | 120 | 1,800 | 2,700 | 45 | 550 |
| 51 | 35 | 65 | <10 | 52 | <10 | 16 |
| 52 | 950 | 2,700 | 220 | 800 | 50 | 250 |
| 53 | 1,600 | 3,300 | 380 | 600 | 260 | 650 |
| 54 | 70 | 100 | 260 | 550 | 550 | 360 |
| 55 | 2,800 | 3,100 | 3,200 | 9,000 | 11,000 | 14,000 |
| 56 | 250 | 460 | | | | |
| 57 | 150 | 220 | 1,100 | 2,800 | 500 | 4,000 |
| 58 | 55 | 120 | 40 | 100 | 85 | 200 |
| 59 | 7,500 | 9,000 | 5,700 | 9,500 | 1,800 | 3,900 |
| 60 | 850 | 1,300 | 9,200 | 20,000 | 700 | 1,500 |
| 61 | 170 | 180 | 1,100 | 5,000 | 120 | 250 |
| 62 | 35 | 64 | 41 | 180 | 55 | 1,800 |
| 63 | 25 | 39 | 52 | 350 | <10 | 45 |
| 64 | | | 800 | 6,000 | 85 | 370 |
| 65 | | | | | 500 | 700 |
| 66 | | | | | | |
| 67 | | | | | | |
| 73 | | | | | | |
| 74 | | | | | | |
| 75 | | | | | | |
| 76 | | | | | | |

| Sub-strate Code # | Proteus mirabilis 1 hr. (cpm) | | Proteus rettgeri 1 hr. (cpm) | | Proteus morganii 1 hr. (cpm) | |
|---|---|---|---|---|---|---|
| | Low | High | Low | High | Low | High |
| 7 | 150 | 290 | 550 | 850 | 320 | 2,100 |
| 10 | 310 | 700 | 210 | 270 | 350 | 620 |
| 18 | 630 | 750 | 5,000 | 6,000 | 510 | 1,400 |
| 19 | 30 | 280 | | <10 | 19 | 51 |
| 20 | 78 | 120 | 20 | 45 | 35 | 52 |
| 21 | 320 | 360 | | <10 | <10 | 20 |
| 22 | 5,200 | 5,800 | 4,000 | 6,000 | 3,900 | 7,100 |
| 23 | <10 | 15 | | <10 | | <10 |
| 24 | 18 | 52 | | <10 | | <10 |
| 25 | 48 | 63 | <10 | 21 | 16 | 28 |
| 26 | 58 | 62 | <10 | 26 | <10 | 62 |
| 27 | <10 | 140 | 220 | 410 | 240 | 260 |
| 28 | | <10 | <10 | 61 | | <10 |
| 29 | 6,500 | 12,000 | 300 | 350 | 1,900 | 2,000 |
| 30 | 7,500 | 10,500 | 4,000 | 5,500 | 3,100 | 5,100 |
| 31 | | | | | | |
| 32 | 7,500 | 9,000 | 950 | 1,900 | 1,200 | 1,400 |
| 33 | 13,000 | 19,000 | 12,000 | 13,000 | 12,000 | 14,000 |
| 34 | 4,000 | 7,100 | 5,600 | 7,400 | 420 | 510 |
| 35 | 3,500 | 5,500 | 16 | 22 | 5,200 | 7,200 |
| 38 | 8,500 | 9,500 | 6,600 | 9,000 | 3,700 | 5,200 |
| 39 | 6,000 | 8,000 | 6,000 | 7,000 | 850 | 3,300 |
| 40 | 1,400 | 1,500 | 4,000 | 6,500 | 5,800 | 6,200 |
| 41 | 9,000 | 21,000 | 8,000 | 9,800 | 5,800 | 7,000 |
| 42 | 850 | 900 | 1,500 | 2,500 | 700 | 2,000 |
| 43 | 9,500 | 10,000 | 2,500 | 3,500 | 4,000 | 4,800 |
| 44 | 8,000 | 9,000 | 8,000 | 8,800 | 6,500 | 7,500 |
| 47 | | | 9,500 | 11,000 | 8,000 | 9,000 |
| 48 | 650 | 780 | 1,100 | 4,700 | 280 | 450 |
| 49 | 65 | 150 | 450 | 1,500 | 75 | 270 |
| 50 | 21 | 90 | 240 | 850 | 120 | 480 |
| 51 | <10 | 21 | 51 | 520 | 12 | 33 |
| 52 | 13 | 280 | 210 | 700 | 120 | 530 |
| 53 | 230 | 1,600 | 2,900 | 4,100 | 1,400 | 2,300 |
| 54 | 140 | 580 | 160 | 1,600 | 140 | 3,100 |
| 55 | 5,000 | 11,000 | 6,500 | 9,200 | 5,000 | 8,800 |
| 56 | 2,400 | 2,800 | 60 | 1,600 | 1,000 | 1,600 |
| 57 | 230 | 310 | 85 | 4,500 | 220 | 580 |
| 58 | 16 | 110 | 100 | 1,600 | <10 | 160 |
| 59 | 1,900 | 3,300 | 1,700 | 4,000 | 2,200 | 5,000 |
| 60 | 12 | 85 | 380 | 2,600 | 270 | 1,700 |
| 61 | 1,800 | 8,500 | 600 | 960 | 75 | 720 |
| 62 | 900 | 2,600 | 96 | 2,100 | 16 | 1,300 |
| 63 | 1,100 | 2,900 | 35 | 550 | <10 | 920 |
| 64 | 650 | 1,900 | 610 | 750 | 34 | 750 |
| 65 | | | | | | |
| 66 | | | | | | |
| 67 | | | | | | |
| 73 | | | | | | |
| 74 | | | | | | |
| 75 | | | | | | |
| 76 | | | | | | |

| Sub-strate Code # | Providence stuartii 1 hr. (cpm) | | Providence alcalifacens 1 hr. (cpm) | | Pseudomonas aeruginosa 1 hr. (cpm) | |
|---|---|---|---|---|---|---|
| | Low | High | Low | High | Low | High |
| 7 | | | | <10 | | <10 |
| 10 | | | 350 | 420 | 370 | 390 |
| 18 | | | 4,800 | 6,200 | 1,600 | 3,800 |
| 19 | | | 40 | 75 | 5,000 | 6,600 |
| 20 | | | 45 | 95 | 100 | 1,600 |
| 21 | | | 65 | 700 | 210 | 230 |
| 22 | | | 2,500 | 4,500 | 1,900 | 2,700 |
| 23 | | | | <10 | 2,700 | 4,800 |
| 24 | | | | <10 | <10 | 28 |

Table 3-continued

| | | | | | |
|---|---|---|---|---|---|
| 25 | | | 31 | 80 | 90 | 100 |
| 26 | | | | <10 | 22 | 56 |
| 27 | | | 250 | 300 | 65 | 8,500 |
| 28 | | | <10 | 18 | 3,500 | 4,000 |
| 29 | | | 2,300 | 7,600 | 5,400 | 6,600 |
| 30 | | | 1,100 | 3,600 | 8,000 | 9,400 |
| 31 | | | | | | |
| 32 | | | 1,200 | 6,200 | 8,000 | 12,000 |
| 33 | | | 9,200 | 11,000 | 5,000 | 9,400 |
| 34 | | | 5,700 | 14,000 | 6,100 | 11,000 |
| 35 | | | 48 | 140 | 4,500 | 5,500 |
| 38 | | | 12,000 | 14,000 | 5,000 | 11,000 |
| 39 | | | 8,500 | 11,000 | 5,800 | 10,500 |
| 40 | | | 6,300 | 16,000 | 880 | 2,200 |
| 41 | | | 13,000 | 15,000 | 8,200 | 11,000 |
| 42 | | | | | 7,600 | 8,300 |
| 43 | | | | | 5,600 | 6,000 |
| 44 | | | 7,500 | 8,000 | 8,800 | 9,200 |
| 47 | | | 14,000 | 15,000 | 8,000 | 10,000 |
| 48 | | | 4,400 | 6,200 | 1,200 | 1,600 |
| 49 | 750 | 900 | 520 | 1,000 | 1,300 | 1,600 |
| 50 | 120 | 130 | 160 | 390 | 1,900 | 2,200 |
| 51 | 180 | 220 | 210 | 370 | 28 | 58 |
| 52 | 380 | 450 | 170 | 1,100 | 100 | 150 |
| 53 | 2,800 | 3,200 | 5,400 | 16,000 | 220 | 280 |
| 54 | 400 | 450 | 280 | 3,200 | 210 | 240 |
| 55 | 6,700 | 7,400 | 3,000 | 6,200 | 3,100 | 3,700 |
| 56 | | | | | | |
| 57 | 260 | 480 | 1,300 | 5,600 | 2,800 | 4,000 |
| 58 | 110 | 180 | 11,000 | 22,000 | 210 | 250 |
| 59 | 5,800 | 6,200 | 11 | 22 | 1,300 | 1,400 |
| 60 | 120 | 160 | 350 | 740 | 5,800 | 6,200 |
| 61 | 570 | 950 | 16 | 280 | 1,500 | 4,000 |
| 62 | 140 | 180 | 80 | 110 | 90 | 230 |
| 63 | 62 | 90 | 26 | 300 | 700 | 2,200 |
| 64 | 140 | 180 | 120 | 180 | 420 | 720 |
| 65 | | | | | | |
| 66 | | | | | | |
| 67 | | | | | | |
| 73 | | | | | | |
| 74 | | | | | | |
| 75 | | | | | | |
| 76 | | | | | | |

The following example illustrates the procedure for the identification of pathogenic bacteria by the radioisotopic identification technique of this invention:

EXAMPLE

A sample of a human stool is received in the laboratory. The history of the patient indicates the possibility of a Salmonella infection. The sample material is streaked onto agar plates including Eosine Methylene Blue Agar, MacConkey Agar, Blood agar, Bismuth Sulfite Agar, Salmonella Shigella agar and Selenite-F Broth. Each inoculated media is then incubated at 35° C. overnight. The next day, the plates are observed and some are found to show bacterial colonies which have the appearance of salmonella. Several typical colonies are picked from the agar plates with a swab and suspended in a saline solution. The cell density is adjusted to an optical density of approximately 1 as determined by a spectrophotometer. About 0.05 ml. of the cell suspension is added dropwise to each well in a microculture tray. Each well on the tray contains 0.05 microcuries of a different one of the following $^{14}C$ labeled substrates identified by the code numbers set forth in Table 2: 7, 18, 19, 20, 21, 22, 23, 24, 25, 27, 28, 30, 33, 34, 35, 40, 42, 43, 44, 47, 50, 53, 55, 57, 58, 59, 60, 61, 62, 63. The inoculated microculture tray is covered with a sheet impregnated with $Ba(OH)_2$, the portion of the cover overlaying each well being coded so as to identify the substrate in that well. The tray is incubated for one hour and the $Ba(OH)_2$ cover is removed and dried under a heat lamp. The microculture tray is discarded into a receptacle for containing radioactive waste materials. The dried $Ba(OH)_2$ containing pad is measured for radioactivity and the counts per minute corresponding to each $^{14}C$ labeled substrate is automatically recorded. There is thereby obtained a radiorespirometric profile of the unknown sample material. This profile is compared to standard radiorespirometric profiles of the organisms set forth in Table 1. Comparison is performed by means of a computer which tests the goodness of fit and statistical reliability. The radiorespirometric profile of the unknown organism is found to compare to the standard radiorespirometric profile of the organism *Salmonella typhi.*

The steps performed on the first day, i.e., the streaking of the sample material on the agar plates followed by overnight incubation, are required by either the conventional or the radiorespirometric indentification technique of this invention. However, the steps performed on the second day for the radioresperometric technique do not require highly experienced personnel which are required by conventional identification techniques since the interpretation of results is not required—i.e., the identification is made automatically. Moreover, the time required to perform the steps on the second day of the radiorespirometric identification technique is about five minutes manipulation time and approximately one hour and 10 minutes total elapsed time which is considerably less than the day or more required by conventional identification techniques.

There will now be described apparatus for collecting and analyzing data relating to a plurality of samples of organisms or the like. A suitable incubation unit assembly for use with an automatic analyzing system is shown in FIGS. 10 and 11 and includes a culture tray 20 having a plurality of generally hemispherical depressions 21 spaced in a regular array of columns and rows throughout the body of the tray. While the tray can be produced as a solid, self-supporting unit similar to that shown in FIGS. 2–4, a relatively inexpensive, disposable and yet equally suitable apparatus can be produced by vacuum forming the tray from a relatively thin sheet of a thermo-formable plastic material. The tray is then designed for use with a reusable support body such as that indicated generally at 23, the support body being relatively thick and rigid and having a plurality of wells 24 spaced in the same array as in tray 20. The upper surface of body 23 is provided with an alignment pin 25 which is designed to pass through an opening 26 provided in tray 20 so that the apparatus will be in proper orientation as well as alignment. The lower surface of body 23 is provided with a plurality of downwardly protruding parallel ribs 27 which extend substantially the length of body 23 and are intended to perform a spacing function during incubation, as will be described.

The apparatus also includes a collection material cover unit indicated generally at 29 which includes a backing member 30 and an absorbent material sheet 31 which constitutes the $CO_2$ collector previously described. The backing member 30 is a relatively stiff plastic member which is generally planar in configuration but which is provided with downwardly extending edges 33 and 34 which serve as stiffeners and as spacers in the analysis system to be described.

As seen in FIG. 11, when the materials are inserted into depressions 21 and the collector material in cover 29 is placed thereon, the assembly constitutes a relatively thin, easily manageable structure in which the cover forms a tight seal over each of the depressions, isolating each such depression from each other depression and from the external atmosphere.

During the incubation period a plurality of such assemblies can be stacked one upon the other as shown in FIG. 12. In that figure, each assembly is spaced from each lower assembly by the downwardly extending ribs 27 to permit the passage of air, thereby maintaining a uniform temperature environment for each incubation unit, regardless of its position in the stack. A weight 35 is placed on the cover 29 of the topmost unit to be sure that the cover of that unit, and all lower units, is tightly covering the depressions in the respective trays 20. Each body 23 can be provided with a legend indicating the time when the incubation for that specific tray is to be terminated so that it can be removed at the appropriate time for further processing and identification procedures.

It will also be observed that the ribs 27, being rather uniformly disposed across the width of each body 23, apply rather uniform pressure to the cover 29 of the unit below it, and that, furthermore, the ribs are disposed beneath rows of wells so that the cover of the unit on which the ribs press is pressed against the well openings, i.e., at exactly the position where pressure is most needed.

As previously described, after the incubation period has transpired the covers are removed and analyzed for level of radioactive material in the specific regions covering the wells. A particularly advantageous apparatus for accomplishing this analysis will now be described.

Figure 13:
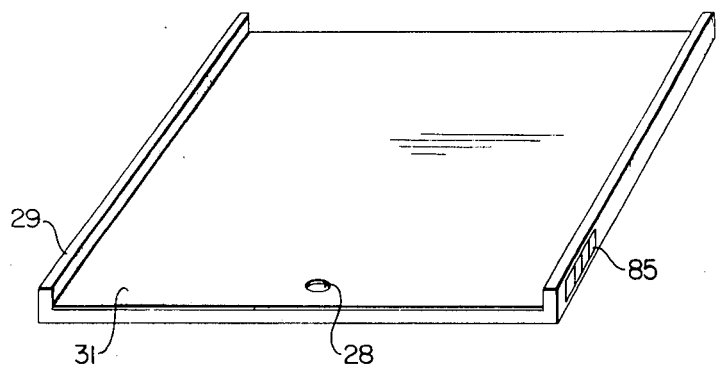
FIGS. 13 and 14 are perspective views of two forms of collection material carriers.

It will be observed, preliminarily, that a cover such as that described for use with the apparatus of FIGS. 10-12 will be that as shown in FIG. 13 wherein a cover 29 is provided with an absorbent layer 31, this being seen from the undersurface or in an inverted position in FIG. 13. The cover is also provided with an alignment hole 28 for alignment with the bodies supporting the material to be analyzed.

Figure 14:
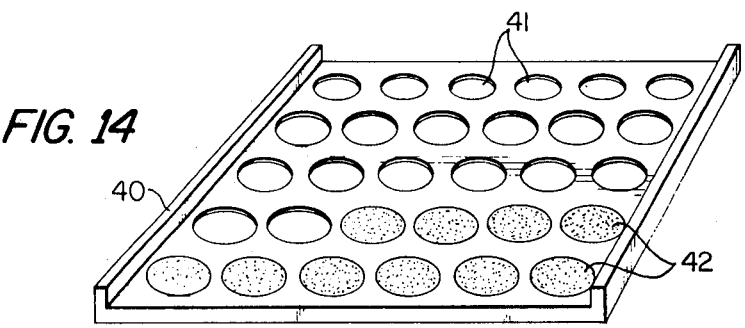

The apparatus to be described, however, is also capable of handling and analyzing materials which have been exposed in a different fashion, specifically in the form of separable pads which can be exposed to a culture and then placed in the cover. For this purpose, a cover of the type shown in FIG. 14 is provided, this constituting a relatively rigid shallow U-shaped tray 40 which is provided with a plurality of depressions 41 to receive pads of absorbent material 42 which are to be investigated. The depressions 41 are shallow and circular and are arranged in regular rows and columns, preferably in the same kind of array employed with depression 24 in body 23 or wells 21 in the culture tray 20 described with reference to FIGS. 10 and 11. Using the same array permits analysis with the same equipment.

Figure 15:
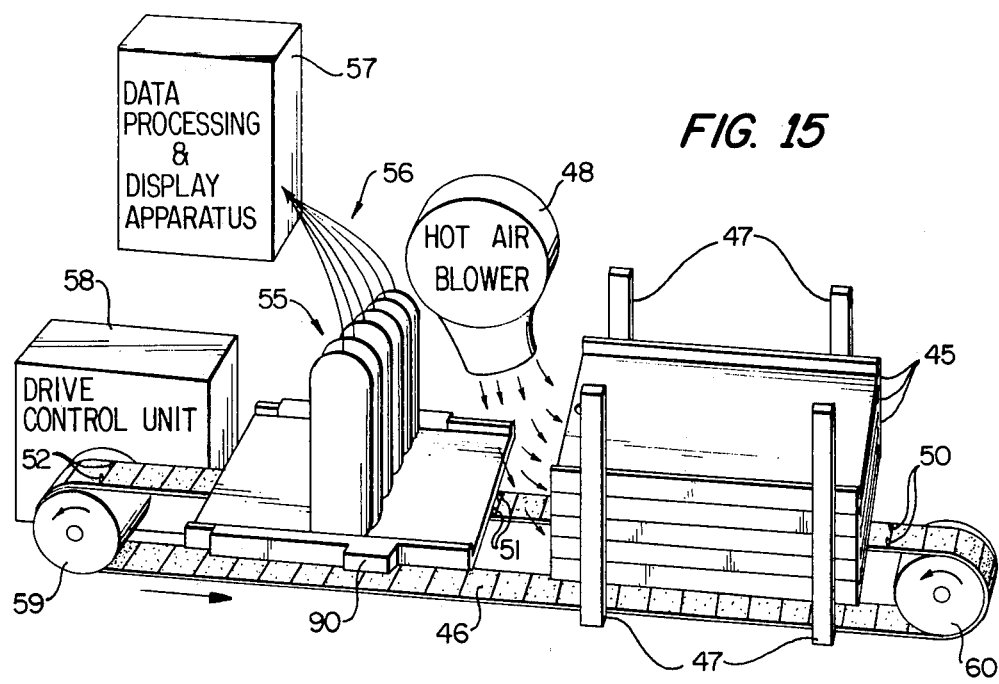
FIG. 15 is a perspective view, partially schematic, of a counting and analysis system usable with the assemblies of FIGS. 10-14.

An automatic apparatus for analyzing the material on the covers is shown in FIG. 15 in a general and schematic fashion. A plurality of covers 45 are stacked one upon the other immediately above a continuous conveyor belt 46. The covers are maintained in aligned position possibly as shown in FIG. 15 between upstanding posts 47. The covers are maintained in spaced relationship by the edges thereof, as shown at 33 and 34 in FIG. 11. It will be observed that the covers can be of the form shown in FIG. 13 or of the form shown in FIG. 14.

A source of hot air 48 is provided in the vicinity of the covers to pass air between the covers, thereby rendering them in a dry state.

The conveyor 46 is provided with sets of upwardly extending lugs in pairs as shown at 50, 51 and 52. The pairs of lugs are spaced apart by distances greater than the length of a cover. When a set of lugs such as 51 arrives at the bottom of one of covers 45, the lugs engage the rear edge of the cover and move it along with the belt past the analyzing apparatus, after which the cover is dropped or removed from the end of the conveyor and either discarded, returned to the input end for a repeat run, or cleaned and prepared for further use.

The analyzing apparatus which is broadly illustrated in FIG. 15 includes a plurality of sensitive detectors indicated generally at 55, these detectors being selected for sensitivity to the specific kind of radioactivity to which the regions of absorbent material 31, or pads 42 have been exposed. In particular, it is contemplated that Geiger-Muller detectors are to be employed and that the number of such tubes is equal to the number of regions in the width of the covers to be inspected. Additionally, the tubes are in the same array as one row of those regions and as one row of wells 21 in sample tray 20.

Detectors 55 produce electrical signals representative of the counts of radioactive particles emitted from the specific regions under examination and those signals are then transmitted over conductors indicated generally at 56 to a data processing and display unit 57 which will be described in greater detail. Generally speaking, however, the data processing apparatus receives the count information from the detectors, compares it with a library of known information describing previously identified material and produces a display, such as a printout, identifying the detected material as one previously identified or indicating that no such valid comparison has been made.

In order for the process of detection and analysis to be properly conducted, it is desirable that each set of regions be moved to a position directly adjacent the detectors 55, be retained in that position for a predetermined interval of time and then moved. It is also desirable that the counters be controlled to read and reset at the beginning and end of each such count, transmitting the count at the reset time. The control of conveyor 46 and the counter is synchronized and performed by a control unit 58 which will also be described in greater detail. Control unit provides the energization of a drive motor 59 and a drive motor 60 which provide the motivating force for conveyor belt 46.

Figure 16:
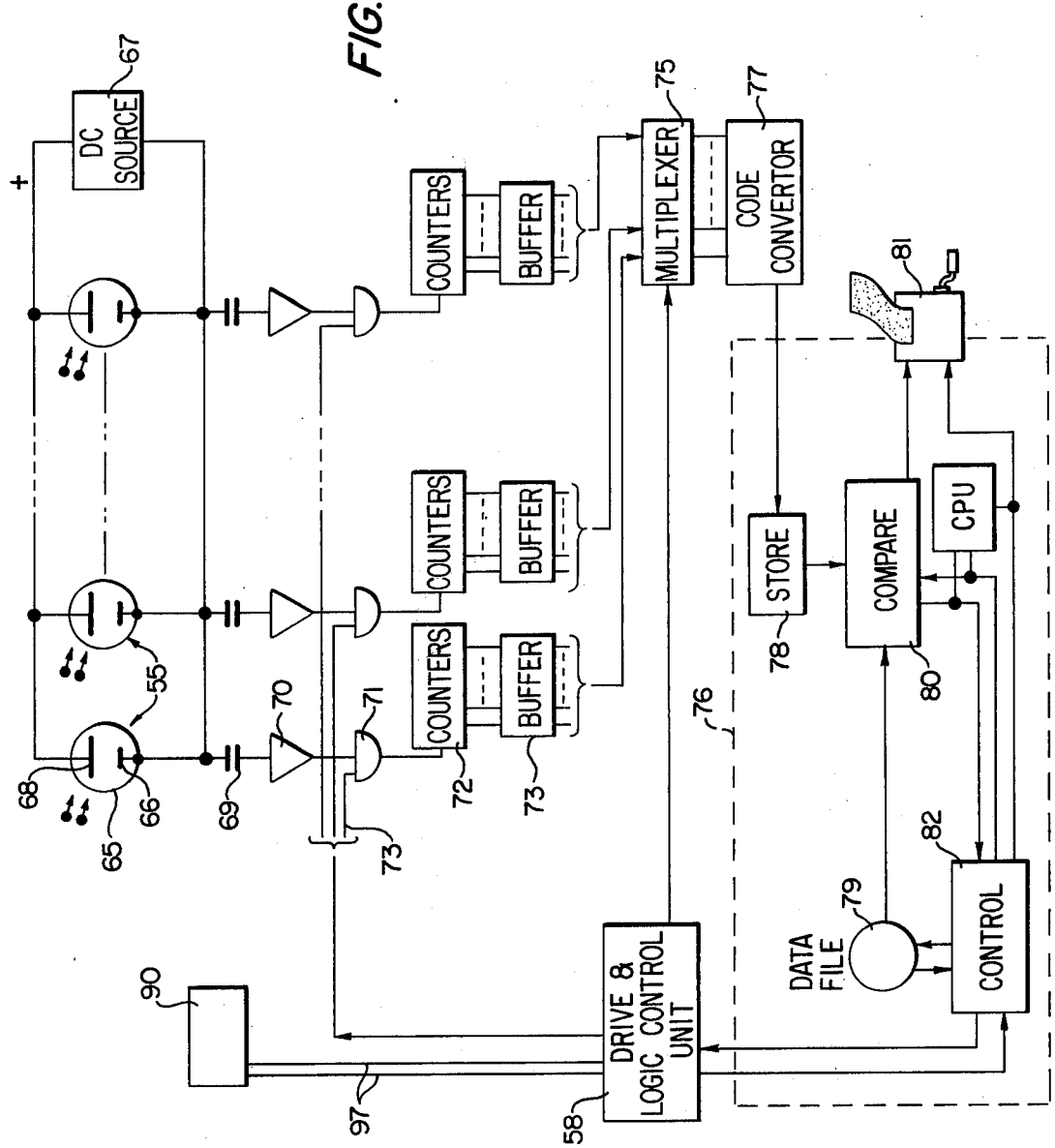
FIG. 16 is a schematic diagram of an analysis and control system usable with the apparatus of FIGS. 10-15.

FIG. 16 shows, in a block schematic diagram form, an apparatus usable in the data processing device referred to in FIG. 15 and used to perform the automatic method of the invention in conjunction with the conveyor and analysis apparatus disclosed therein. A plurality of particle detectors are indicated generally at 55, each of these being connected to a source of D.C. voltage which is conventionally required, the voltage being a relatively high voltage in the case of the usual Geiger-Muller tubes. One such tube and the apparatus used therewith will be described in detail. The remaining tubes are provided with substantially identical processing channels.

Each tube includes an envelope 65 which contains an ionizable gas, the envelope surrounding an electrode 66 connected to one terminal of the D.C. source 67. The other terminal of the source is connected to an electrode 68 which extends into the ionizable gas and detects the avalanche ionization activity indicative of the exposure of the device to a particle. Each such activity generates a pulse electrical output which is coupled through a capacitor 69 to the input of a conventional amplifier 70 which can be employed to strengthen the signal and, if desired, to perform a shaping function.

The output of amplifier 70 is connected through an AND gate 71 to the input of a counter 72 which receives the pulses gates through from amplifier 70 and accumulates a count thereof. The output of the counter can be transferred to a buffer storage unit 74 for temporary storage of the count, rendering it available to further processing apparatus.

A drive control unit 58 operates in conjunction with a sequence control or multiplying apparatus 75 and includes timing devices to activate the various portions of the system in proper order. As described previously in connection with the method of the present invention, it is desirable to accumulate a count representative of the mean rate of emission of particles from each region of the absorbent material being investigated. Thus, it is necessary to control the interval of time during which each tube is exposed to each specific region from which a radiation count is to be obtained. This interval is controlled by AND gate 71 and the input to the AND gate on conductor 73, which input is provided from control circuitry within control unit 58. That control unit opens gate 71, permitting pulses to be delivered to the counters only during the predetermined interval.

Control unit 58 also provides signals to the sequence selector or multiplexor 75 to permit the sequence selector to transfer accumulated count information from the buffer 74 and the similar buffers associated with the other Geiger-Muller tubes in the sensor array, the counts being individually provided to a computer 76 which further processes the information and provides a usable result. The function of the sequence selector is to provide the accumulated counts in an established, ordered sequence so that they can be further analyzed. If necessary, the count selected by the sequence selector can be provided to a translator 77, the function of which is recognizable by the computer. The transmitted information is then inserted into a store 78 within the computer and it is compared with previously stored information contained in a data file library 79, the comparison being accomplished in a word comparator 80. The results of the comparison, including the identification of all matches occurring between the data in store 78 and library 79, is printed or otherwise displayed in a read out unit 81 of conventional nature. The comparison operation and the control of the library scan and coordination of these operations with the sequencer are accomplished by an internal control unit 82 which provides control signals and receives accomplishment feedback signals from the comparison unit, the library and control unit 58.

As previously indicated, the analysis system described herein is capable of performing analysis of various types. In order for the data processing apparatus to appropriately function, it is necessary that reference be made, for example, to the appropriate library, and it is further necessary for the control and comparison apparatus to be provided with appropriate start-up information so that the appropriate libraries can be searched, among other things. To render this aspect of the operation as automatic as possible, each one of covers 45 provided to the unit is identified by a code plate 85 disposed on an edge of each cover. The code plate is a relatively simple device which permits each cover to be readily identified as to test type as well as with other information. One such code plate, and a system of reading the plate usable with the apparatus of FIG. 15, is shown in FIGS. 17–19. In FIG. 17 the edge of a cover 29 is provided with a code plate indicated generally at 85 including a plurality of reflective rectangles 86, each such rectangle being adhered to a release paper backing 87 mounted on cover 29. The rectangles can be formed by scribing line 88 at regular intervals in a continuous reflective strip. While only four rectangles are shown in FIG. 17, it will be apparent that a much larger number of rectangles can be used, depending upon the number of bits required for a specific identification purpose. The entire plate can be removed and replaced for reuse of the cover if desired.

The coding operation takes place by simply removing a selected number of the reflective rectangles in specific positions, thereby forming a digital word in which reflective and nonreflective rectangles are established in a specific sequence. The rectangles can be arrayed in this manner in accordance with a preestablished code identifying the operation to be accomplished with that cover. One partly peeled label is shown at 89. If that label were to be removed completely leaving the other three reflective rectangles in place, and if a system is established in which a reflective rectangle represents a binary 1 and the absence thereof indicates a binary zero, the word formed by the removal of rectangle 89 would be 1101.

It is contemplated that the code plate would be positioned near the front end of a cover 29 as shown at 85 in FIG. 13. An optical reader housing 90 can then be disposed at one end of a guide rail through which the cover will pass so that the cover code can be read and the information contained therein employed before the Geiger tubes begin to gather data from the regions on the cover. A typical optical apparatus which can be employed to accomplish this function is shown in FIGS. 18 and 19 wherein a housing 90 is mounted on a guide rail 91 and contains a source of light 92, the source of energization for which is conventional and not shown. A photoelectrical cell 93 is also disposed in housing 90, the source and cell being separated by an opaque barrier 94. An opening 95 permits light to emerge from the housing containing source 92 and an opening 96 permits light reflected from code plate 85 to enter the housing and impinge upon cell 93, producing an electrical variation which will be recognized by appropriate photo cell circuitry as the existence of a digital bit. A sequence of such of bits can be provided to control apparatus 58 by conductors 97 as the cover moves past the reader to initiate the necessary control functions.

Specifically, assume that code 1101 identifies a cover having regions of collected $CO_2$ from an unknown organism which has been incubated with a plurality of known substrates 1 through 36 in table. Receipt of code 1101 by control unit 58 will (1) cause that control unit to drive the conveyor past detectors 55 in a stepwise fashion, pausing with each detector over its region for a predetermined interval suitable for that test; (2) indicate to control 82 that the data file set for all count ranges resulting from tests with substrates 1 through 36 should be made available for comparison with count data to be provided to store 78; and (3) activate a subroutine to receive each count in multiplexed sequence from sequencer 75, compare it with each item in the relevant set in the data file, and print out the count and match identification whenever a match occurs, i.e., whenever the count read from a particle detector falls within one of the count ranges in the data file set.

This is a relatively simple sequence of events which will yield basis data on which a first sort can be made. In most cases, this data will indicate a number of organisms which the unknown cannot, or probably would not, be, and may also indicate most suitable substrates to use in a second set of tests in a second tray. The second test would follow substantially the same steps as the first except that the code established on plate 85 will indicate to the control unit that a different set of substrates is being employed with the unknown microorganism and that a different data file set is to be used for comparison. This sequence of steps can be repeated, as necessary until a sufficiently accurate match with a sufficiently large number of substrates identifies the organism to a required degree of certainty or specificity.

A more sophisticated, more accurate and faster, but somewhat more complex, approach involves the use of the matching and computing capacity of the computer central processing unit (CPU). In this technique, a second data file, which can be a read out only memory, is provided with permutations of matches which identify organisms to various degrees of completeness in accordance with known statistical procedures. The apparatus can then be queried regarding the identity of an organism tested on, for example, a set of six trays with an assortment of substrates, to a probability expressed in sigma functions. The resulting printout will then be programmed to yield each such organism identity, if more than one exist, which satisfy the requested accuracy.

While certain advantageous embodiments of the invention have been chosen to illustrate the invention, it will be understood by those skilled in the art that various changes and modifications can be made therein without departing from the scope of the invention as defined in the appended claims.

I claim:

1. An apparatus for identifying a microorganism from radioactive trace material comprising the combination of
    means for individually incubating samples of the microorganism with a plurality of preselected substrates each having radioactive trace material therein;
    means for collecting gaseous material evolved from the means for incubating in zones arranged in a predetermined pattern, said means for collecting being removable from said means for incubating after incubation;
    means for storing a plurality of said means for collecting after removal thereof from said means for incubating;
    a plurality of radioactive particle detectors;
    conveyor means for individually transporting said means for collecting from said means for storing along a path;
    means for mounting said radioactive particle detectors adjacent said path in an array similar to a segment of said pattern;
    means for controlling and driving said conveyor means to move each said means for collecting to a location along said path at which a first segment of zones in said pattern is adjacent said detectors, to pause at said location, and to then sequentially move the positions at which each segment of zones are successively exposed to said detectors;
    means electrically connected to each of said detectors for accumulating a count of radioactive particles detected by each detector at each zone;
    means for storing a record of counts representative of known microorganisms incubated in known substrates;
    means for comparing a plurality of said known counts with a plurality of counts derived from said detectors and for displaying the results of the comparisons.

2. An apparatus according to claim 1 wherein said means for incubating includes
    a disposable tray having a plurality of depressions formed therein; and
    a relatively rigid support body having a plurality of depressions formed in a major surface thereof in a pattern identical to said tray so that said tray can be placed in mating relationship with said body.

3. An apparatus according to claim 2 wherein the pattern of depressions in said tray and said body forms parallel lines,
    said body further comprising a plurality of parallel ribs protruding from a surface parallel to said major surface,
    said ribs being formed along lines parallel to said lines defined by said pattern of depressions.

4. An apparatus according to claim 2 wherein said means for collecting includes
    a planar sheet of getter material; and
    support means for said sheet, said support means including
    a cover having side edges extending from one face thereof, said getter material being adhered to said one face.

5. An apparatus for identifying a microorganism from radioactive trace material comprising the combination of
    means for incubating samples of the microorganism with a plurality of preselected substrates each having radioactive trace material therein, said means for incubating including
    a disposable tray having a plurality of depressions formed therein, and
    a relatively rigid support body having a plurality of depressions formed in a major surface thereof in a pattern identical to said tray so that said tray can be placed in mating relationship with said body;
    means for collecting gaseous material evolved from the means for incubating in zones arranged in a predetermined pattern, said means for collecting including
    a planar sheet of getter material,
    support means for said sheet, said support means including a cover having side edges extending from one face thereof, said getter material being adhered to said one face, and electromagnetic radiation reflecting means attached to an outer surface of one of said side edges of said cover;
    means for storing a plurality of said means for collecting;
    a plurality of radioactive particle detectors,
    conveyor means for individually transporting said means for collecting from said means for storing along a path, said conveyor means including
    a source of electromagnetic radiation,
    radiation responsive means for detecting reflected radiation from said source and for producing electrical signals representative thereof; and means for mounting said source and responsive means in a position to illuminate and receive reflections from said reflecting means as said tray approaches said radioactive particle detectors, said reflecting means being changeable to identify the nature of the analysis to be performed;

means for mounting said ratioactive particle detectors adjacent said path in an array similar to a segment of said pattern;

means for controlling and driving said conveyor means to move each said means for collecting to a location along said path at which a first segment of zones in said pattern is adjacent said detectors, pause at said location; and then sequentially move to positions at which each segment of zones are exposed to said detectors;

means electrically connected to each of said detectors for accumulating a count of radioactive particles detected by each detector at each zone;

means for storing a record of counts representative of known microorganisms incubated in known substrates;

means for comparing a plurality of said known counts with a plurality of counts derived from said detectors and for displaying the results of the comparisons.

6. An apparatus for identifying a microorganism from radioactive trace material comprising the combination of means for incubating samples of the microorganism with a plurality of preselected substrates each having radioactive trace material therein;

means for collecting gaseous material evolved from the means for incubating in zones arranged in a predetermined pattern; means for storing a plurality of said means for collecting; a plurality of radioactive particle detectors;

conveyor means for individually transporting said means for collecting from said means for storing along a path;

means for mounting said radioactive particle detectors adjacent said path in an array similar to a segment of said pattern;

means for controlling and driving said conveyor means to move each said means for collecting to a location along said path at which a first segment of zones in said pattern is adjacent said detectors, pause at said location; and then sequentially move to positions at which each segment of zones are exposed to said detectors;

means electrically connected to each of said detectors for accumulating a count of radioactive particles detected by each detector at each zone;

means for storing a record of counts representative of known microorganisms incubated in known substrates;

means for comparing a plurality of said known counts with a plurality of counts derived from said detectors and for displaying the results of the comparisons;

said means for storing comprising a plurality of upstanding parallel guide members on opposite sides of said path to define a vertical chute in which said means for collecting can be stacked; said conveyor means comprising an endless band having a plurality of protruding lugs for engaging the bottom one of said means for collecting stacked between said guide members.

* * * * *